United States Patent
Sánchez Casals et al.

(10) Patent No.: US 11,325,911 B2
(45) Date of Patent: May 10, 2022

(54) METHOD FOR PREPARING 3-[(4S)-8-BROMO-1-METHYL-6-(PYRIDIN-2-YL)-4H-IMIDAZO[1,2-A][1,4]BENZODIAZEPIN-4-YL]-PROPIONIC ACID METHYL ESTER, AND COMPOUNDS USEFUL IN SAID METHOD

(71) Applicant: MOEHS IBERICA, S.L., Rubí-Barcelona (ES)

(72) Inventors: Carles Sánchez Casals, Rubí-Barcelona (ES); Alicia Dobarro Rodríguez, Rubí-Barcelona (ES)

(73) Assignee: MOEHS IBERICA, S.L.

( * ) Notice: Subject to any disclaimer, the term of this patent is extended or adjusted under 35 U.S.C. 154(b) by 34 days.

(21) Appl. No.: 16/754,821

(22) PCT Filed: Oct. 11, 2018

(86) PCT No.: PCT/EP2018/077669
§ 371 (c)(1),
(2) Date: Apr. 9, 2020

(87) PCT Pub. No.: WO2019/072944
PCT Pub. Date: Apr. 18, 2019

(65) Prior Publication Data
US 2020/0239477 A1    Jul. 30, 2020

(30) Foreign Application Priority Data
Oct. 13, 2017 (ES) .................. ES201731210

(51) Int. Cl.
*C07D 487/04* (2006.01)
*A61P 25/20* (2006.01)
*C07D 401/04* (2006.01)
*C07D 413/14* (2006.01)

(52) U.S. Cl.
CPC ......... *C07D 487/04* (2013.01); *C07D 401/04* (2013.01); *C07D 413/14* (2013.01)

(58) Field of Classification Search
CPC .. C07D 487/04; C07D 401/04; C07D 413/14; A61P 25/20
See application file for complete search history.

(56) References Cited

U.S. PATENT DOCUMENTS

| | | |
|---|---|---|
| 4,001,261 A | 1/1977 | Gall |
| 2016/0009680 A1 | 1/2016 | Kawakami et al. |
| 2017/0044135 A1 | 2/2017 | Tilbrook et al. |

FOREIGN PATENT DOCUMENTS

| | | | |
|---|---|---|---|
| DE | 2647176 A1 | 4/1977 | |
| WO | 2011032692 A1 | 3/2011 | |
| WO | 2018148361 A1 | 8/2018 | |
| WO | WO-2019020790 A1 * | 1/2019 | ........... C07D 487/04 |

OTHER PUBLICATIONS

International Search Report, dated Jun. 12, 2018 for International Application No. PCT/EP2018/077669.

* cited by examiner

*Primary Examiner* — Samira J Jean-Louis
(74) *Attorney, Agent, or Firm* — Tristan A. Fuierer; Casimir Jones, S.C.

(57) ABSTRACT

The present invention relates to a method for preparing 3-[(4S)-8-bromo-1-methyl-6-(pyridin-2-yl)-4H-imidazo[1,2-a] [1,4]benzodiazepin-4-yl]-propionic acid methyl ester starting from 3-[(3S)-7-bromo-2-oxo-5-(pyridin-2-yl)-2,3-dihydro-1H-[1,4]-benzodiazepin-3-yl] propionic acid methyl ester, and novel compounds useful as intermediates in said method, i.e., (3S)-3-[7-bromo-2-(2,2-dimethoxypropylamino)-5-pyridin-2-yl-3H-benzo[e] [1,4]diazepin-3-yl] propionic acid methyl ester.

4 Claims, 11 Drawing Sheets

METHOD FOR PREPARING 3-[(4S)-8-BROMO-1-METHYL-6-(PYRIDIN-2-YL)-4H-IMIDAZO[1,2-A][1,4]BENZODIAZEPIN-4-YL]-PROPIONIC ACID METHYL ESTER, AND COMPOUNDS USEFUL IN SAID METHOD

CROSS-REFERENCE TO RELATED APPLICATIONS

This application is filed under the provisions of 35 U.S.C. § 371 and claims the priority of International Patent Application No. PCT/EP2018/077669 filed on 11 Oct. 2018 entitled "METHOD FOR PREPARING 3-[(4S)-8-BROMO-1-METHYL-6-(PYRIDIN-2-YL)-4H-IMIDAZO[1,2-A][1,4]BENZODIAZEPIN-4-YL]-PROPIONIC ACID METHYL ESTER, AND COMPOUNDS USEFUL IN SAID METHOD" in the name of Carles SÁNCHEZ CASALS, et al., which claims priority to Spanish Patent Application No. P201731210, filed on 13 Oct. 2017, both of which are hereby incorporated by reference herein in their entirety.

FIELD OF THE INVENTION

The present invention relates to a method for preparing 3-[(4S)-8-bromo-1-methyl-6-(pyridin-2-yl)-4H-imidazo[1,2-a] [1,4]benzodiazepin-4-yl]-propionic acid methyl ester starting from 3-[(3S)-7-bromo-2-oxo-5-(pyridin-2-yl)-2,3-dihydro-1H-[1,4]-benzodiazepin-3-yl] propionic acid methyl ester, and to novel compounds useful as intermediates in said method.

BACKGROUND OF THE INVENTION

International patent application WO 00/69836 describes short-acting [1,4]-benzodiazepines which include a carboxylic ester moiety and are inactivated by non-specific tissue esterases. An organ-independent elimination mechanism is predicted to be characteristic of these benzodiazepines, providing a more predictable and reproducible pharmacodynamic profile. The compounds are suitable for therapeutic purposes, including sedative-hypnotic, anxiolytic, muscle relaxant, and anticonvulsant purposes. The compounds are short-acting CNS depressants that are useful to be administered intravenously in the following clinical settings: preoperative or intensive care unit sedation, anxiolysis, and amnestic use for perioperative events; conscious sedation during short diagnostic, operative, or endoscopic procedures; as a component for the induction and maintenance of general anesthesia, prior and/or concomitant to the administration of other anesthetic or analgesic agents.

Example Ic-8 of patent document WO 00/69836 describes a general method for preparing benzodiazepine derivatives, such as 3-[(4S)-8-bromo-1-methyl-6-(pyridin-2-yl)-4H-imidazo[1,2-a] [1,4]benzodiazepin-4-yl]-propionic acid methyl ester of formula (F) from lactam of formula (D).

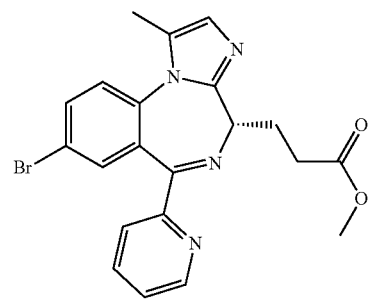

(F)

In turn, it also describes the method of preparation of lactam (D) from precursor (A). Said method consists of reacting (2-amino-5-bromo-phenyl)-pyridin-2-yl-methanone of formula (A) with (2S)-2-(fluorenyl-9-methoxycarbonylamino)-5-methoxy-5-oxo-pentanoic acid chloride, yielding the amide of formula (B1).

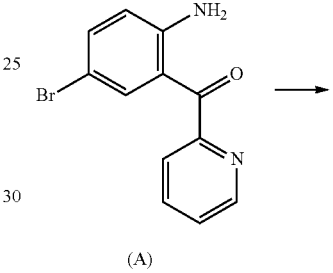

(A)

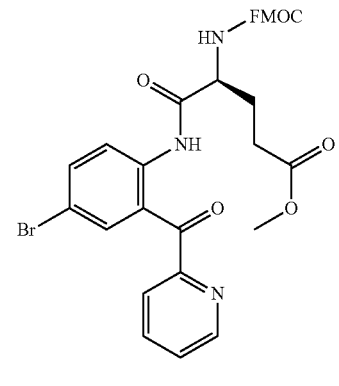

(B1)

The document teaches that the treatment of B1 with triethylamine in dichloromethane followed by treatment with acetic acid in dichloromethane yields lactam, 3-[(3S)-7-bromo-2-oxo-5-(pyridin-2-yl)-2,3-dihydro-1H-[1,4]-benzodiazepin-3-yl] propionic acid methyl ester of formula (D).

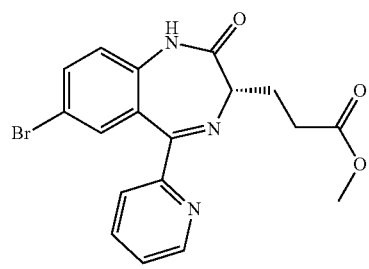

(D)

The method of obtaining (F) according to WO 00/69836 consists of reacting the compound of formula (D) with a suspension of NaH in THF, treating the reaction mixture with bis-morpholinophosphorylchloride (BMPC, Ning et al., J Org. Chem. 1976, 41, 2720-2724; Ning et al., J Org. Chem. 1976, 41, 2724-2727) in THF, filtering the reaction mixture, reacting the filtrate with DL-1-amino-2-propanol, purifying the alcoholic adduct obtained, treating said purified alcoholic adduct with a mixture of DMSO and oxalyl chloride in dichloromethane, treating the reaction mixture with triethylamine, diluting with ethyl acetate, washing with aqueous solutions, and concentrating them to yield a foam, treating said foam with a catalytic amount of p-toluenesulfonic acid, neutralizing the solution with sodium bicarbonate, and isolating the compound of formula (F).

However, the method comprises a large number of steps, resulting in insufficient optical purity of the compounds obtained in the different steps and a low overall yield. For these reasons, the method of WO 00/69836 is not satisfactory for production on an industrial level.

International patent application WO 2011/032692 likewise describes the method for synthesizing [1,4]-benzodiazepine of formula (F), as well as the benzenesulfonic acid salt thereof, from the lactam of formula (D).

In this case, the synthesis pathway of the lactam of formula (D) likewise starts from (2-amino-5-bromo-phenyl)-pyridin-2-yl-methanone of formula (A), but (A) is reacted with glutamate protected with tBoc (tert-butyloxycarbonyl), yielding methyl (4S)-4-(tert-butyloxycarbonylamino)-5-[4-bromo-2-(pyridine-2-carbonyl)aniline]-5-oxo-pentanoate of formula (B). The deprotection of the amide of formula (B) is performed by means of treatment with HCl, yielding methyl (4S)-4-amino-5-[4-bromo-2-(pyridine-2-carbonyl)aniline]-5-oxo-pentanoate hydrochloride salt of formula (C).

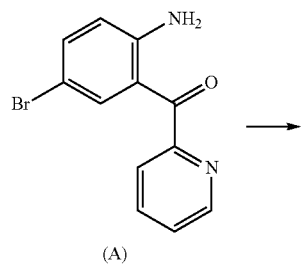

(A)

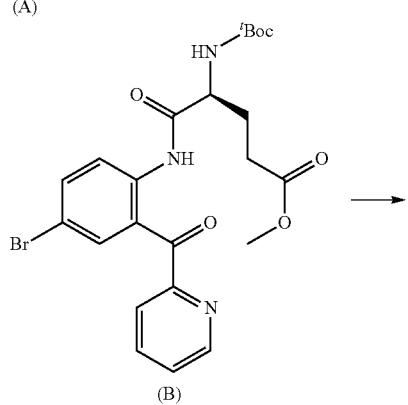

(B)

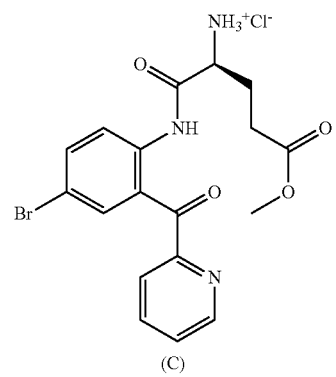

(C)

In WO 2011/032692, the treatment of (C) with a base yields the cyclized compound of formula (D), lactam 3-[(3S)-7-bromo-2-oxo-5-(pyridin-2-yl)-2,3-dihydro-1H-[1,4]-benzodiazepin-3-yl] propionic acid methyl ester. The lactam of formula (D) is reacted with lithium diisopropylamide (LDA) and bis-morpholinophosphorylchloride (BMPC) to yield 3-[(3S)-7-bromo-2-(bis-morpholinophosphoryloxy)-5-(pyridin-2-yl)-3H-[1,4]-benzodiazepin-3-yl]-propionic acid methyl ester of formula (E1). The latter is reacted with (R)-1-amino-2-propanol or (S)-1-amino-2-propanol in aprotic solvent to yield 3-[(S)-7-bromo-2-((R and/ or S)-2-hydroxy-propylamino)-5-(pyridin-2-yl)-3H-[1,4]-benzodiazepin-3-yl]-propionic acid methyl ester of formula (EM).

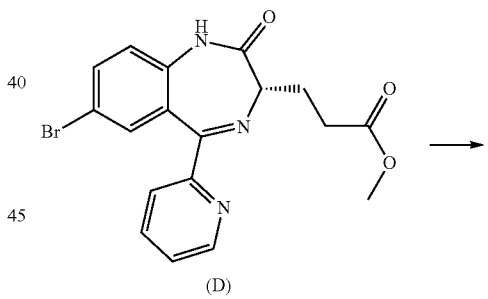

(D)

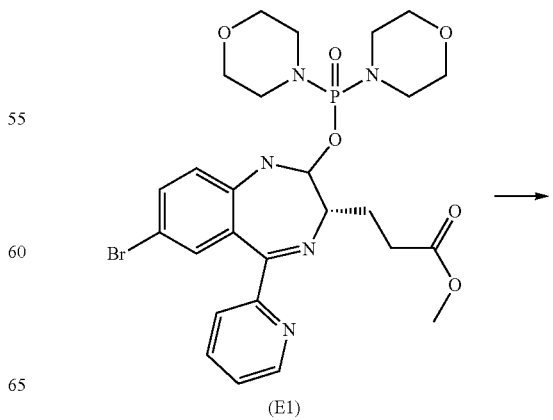

(E1)

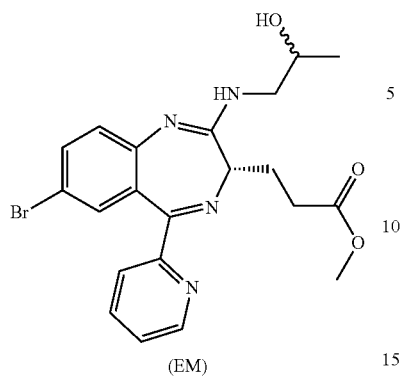

(EM)

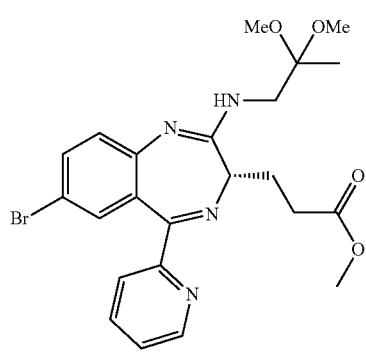

(E2)

Nevertheless, to obtain 3-[(4S)-8-bromo-1-methyl-6-(pyridin-2-yl)-4H-imidazo[1,2-a] [1,4]benzodiazepin-4-yl]-propionic acid methyl ester of formula (F), patent document WO 2011/032692 discloses as an example a complex and dangerous reaction of the compound of formula (EM) with Dess-Martin periodinane, an explosive oxidation agent, in acidic medium.

The distinguishing feature of the process developed by the inventors is the use of a primary amine comprising an acetal group (compared to (R)-1-amino-2-propanol of WO2011/032692A) to obtain an intermediate of general formula (E)

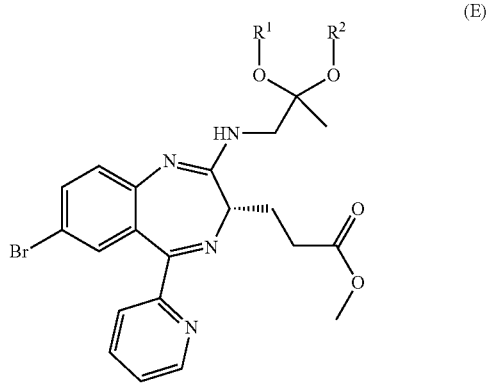

(E)

wherein $R^1$ and $R^2$ are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein $R^1$, together with $R^2$, forms a residue of formula —CH$_2$—(CR$^3$R$^4$)$_n$—CH$_2$—, wherein n is equal to 0, 1, 2, 3, or 4, and wherein $R^3$ and $R^4$ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl.

In an embodiment of the present invention, the compound of formula E is intermediate (3S)-3-[7-bromo-2-(2,2-dimethoxypropylamino)-5-pyridin-2-yl-3H-benzo[e] [1,4]diazepin-3-yl]propionic acid methyl ester of formula (E2) obtainable by means of using 2,2-dimethoxypropylamine as a primary amine, which is readily isolatable and can be purified when required. The presence of the acetal of said intermediate yields a synthesis of (F), or its pharmaceutically acceptable salts, without requiring subsequent treatment with an oxidizer, since it is the actual acid that is used that allows performing hydrolysis of the acetal, subsequent cyclization, and finally obtaining the corresponding salt of the compound of formula (F), also known as remimazolam.

BRIEF DESCRIPTION OF THE INVENTION

The authors of the present invention have developed a novel method for synthesizing the product of formula (F), with less complicated reagents, significantly higher reaction yields and providing products having a higher purity than the methods described in the state of the art. The key point of the invention is to provide a novel method for synthesizing the compound of formula (F), or pharmaceutically acceptable salts thereof, starting from the compound of formula (E) but via an alternative intermediate (improving the overall yield of the synthesis) to the compound of formula (EM).

Therefore, a first aspect of the invention relates to a method for preparing 3-[(4S)-8-bromo-1-methyl-6-(pyridin-2-yl)-4H-imidazo[1,2-a] [1,4]benzodiazepin-4-yl]-propionic acid methyl ester of formula (F),

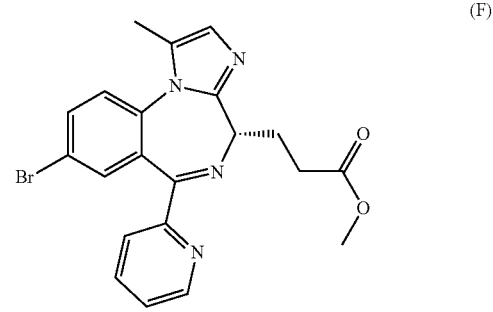 [SMILES: COC(=O)CC[C@@H]1N=C(c2ccccn2)c2cc(Br)ccc2-n2c(C)cnc21]

(F)

or a pharmaceutically acceptable salt, characterized in that it comprises the step of reacting a compound of formula (E),

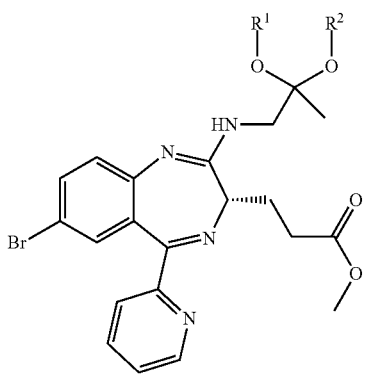

wherein R¹ and R² are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein R¹, together with R², forms a residue of formula —CH₂—(CR³R⁴)$_n$—CH₂—, wherein n is equal to 0, 1, 2, 3, or 4, and wherein R³ and R⁴ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; with an acid.

In a particular embodiment of the first aspect, the invention relates to a method for preparing 3-[(4S)-8-bromo-1-methyl-6-(pyridin-2-yl)-4H-imidazo[1,2-a][1,4]benzodiazepin-4-yl]-propionic acid methyl ester of formula (F),

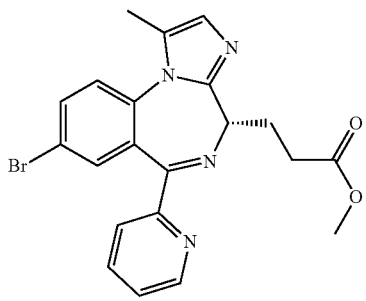

or a pharmaceutically acceptable salt, characterized in that it comprises the step of reacting (3S)-3-[7-bromo-2-(2,2-dimethoxypropylamino)-5-pyridin-2-yl-3H-benzo[e][1,4]diazepin-3-yl]propionic acid methyl ester of formula (E2)

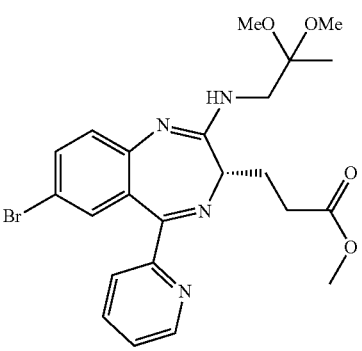

with an acid.

In another particular embodiment of the first aspect, the invention relates to a method for preparing the besylate of 3-[(4S)-8-bromo-1-methyl-6-(pyridin-2-yl)-4H-imidazo[1,2-a][1,4]benzodiazepin-4-yl]-propionic acid methyl ester of formula (F),

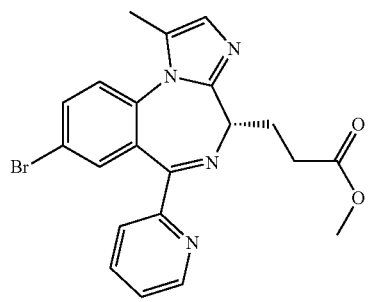

characterized in that it comprises the step of reacting a compound of formula (E),

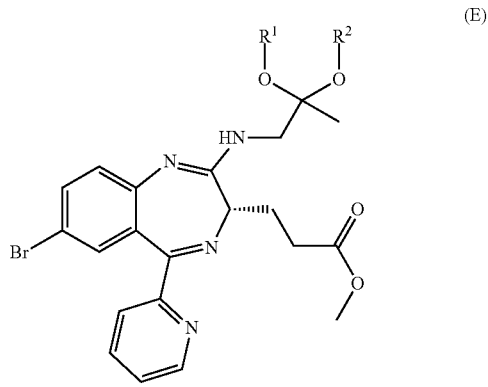

wherein R¹ and R² are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein R¹, together with R², forms a residue of formula —CH₂—(CR³R⁴)$_n$—CH₂—, wherein n is equal to 0, 1, 2, 3, or 4, and wherein R³ and R⁴ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; with benzenesulfonic acid.

In a second aspect, the invention relates to a method for preparing a compound of formula (E),

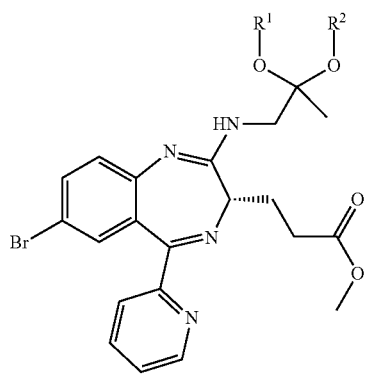

wherein R¹ and R² are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein R¹, together with R², forms a residue of formula —CH₂—(CR³R⁴)ₙ—CH₂—, wherein n is equal to 0, 1, 2, 3, or 4, and wherein R³ and R⁴ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; characterized in that it comprises the step of reacting the compound of formula (DE)

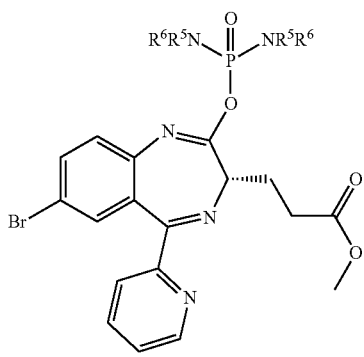

(DE)

wherein R⁵ and R⁶ are independently selected from a linear or branched C1-C4 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein R⁵ and R⁶ adjacent to one another form a saturated 4- to 7-membered heterocycle with the nitrogen to which they are bound, and wherein the heterocycle optionally contains 1, 2, or 3 heteroatoms selected from N and O;
with a primary amine of formula,

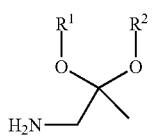

wherein R¹ and R² are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein R¹, together with R², forms a residue of formula —CH₂—(CR³R⁴)ₙ—CH₂—, wherein n is equal to 0, 1, 2, 3, or 4, and wherein R³ and R⁴ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl.

In a particular embodiment of the second aspect, the invention relates to a method for preparing (3S)-3-[7-bromo-2-(2,2-dimethoxypropylamino)-5-pyridin-2-yl-3H-benzo[e][1,4]diazepin-3-yl]propionic acid methyl ester of formula (E2)

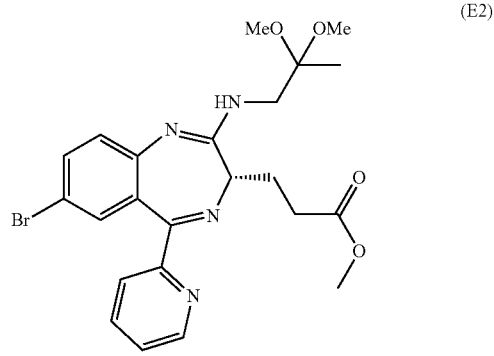 [SMILES: COC(=O)CC[C@@H]1N=C(c2ccccn2)c2cc(Br)ccc2N=C1NCC(C)(OC)OC]

(E2)

characterized in that it comprises the step of reacting the compound of formula (E1)

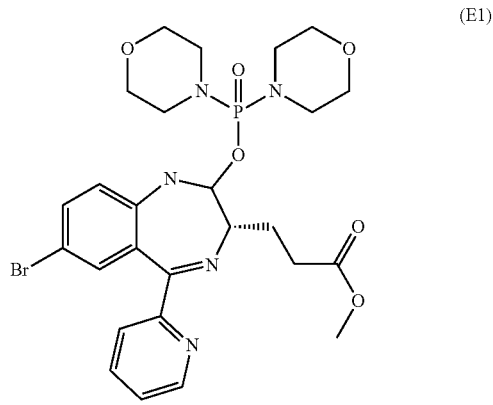 [SMILES: COC(=O)CC[C@@H]1N=C(c2ccccn2)c2cc(Br)ccc2NC1OP(=O)(N1CCOCC1)N1CCOCC1]

(E1)

with 2,2-dimethoxy-propylamine.

In a third aspect, the present invention relates to the use of the compound of formula (E),

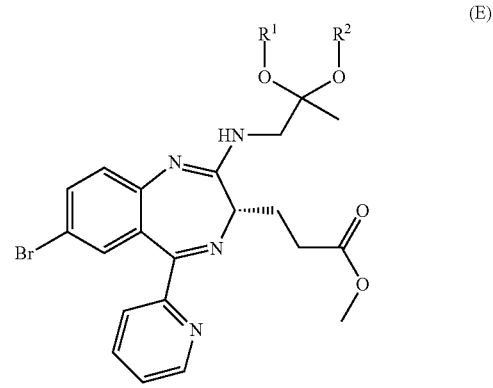

(E)

wherein R¹ and R² are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein $R^1$, together with $R^2$, forms a residue of formula —CH$_2$—(CR$^3$R$^4$)$_n$—CH$_2$—, wherein n is equal to 0, 1, 2, 3, or 4, and wherein $R^3$ and $R^4$ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl;

for preparing a compound of formula (F)

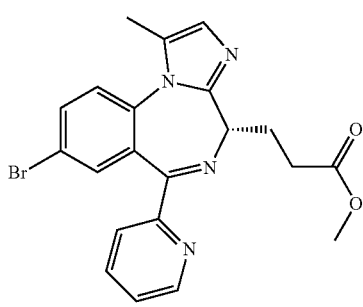

or a pharmaceutically acceptable salt.

In a particular embodiment of the third aspect, the present invention relates to the use of (3S)-3-[7-bromo-2-(2,2-dimethoxypropylamino)-5-pyridin-2-yl-3H-benzo[e] [1,4]diazepin-3-yl]propionic acid methyl ester of formula (E2)

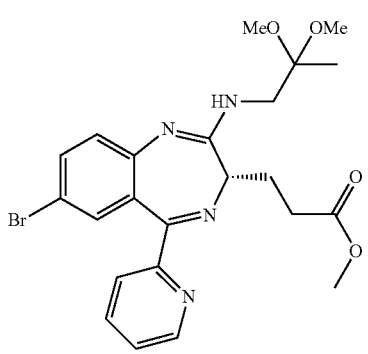

for preparing a compound of formula (F)

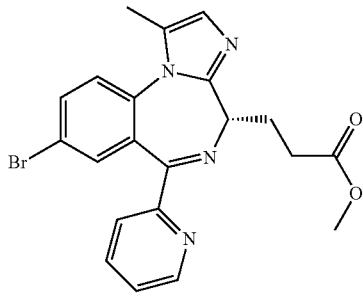

or a pharmaceutically acceptable salt.

In a fourth aspect, the present invention relates to the use of the compound of formula (DE)

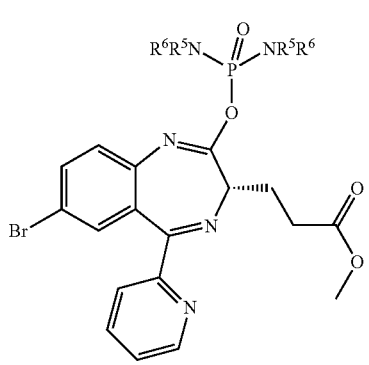

wherein $R^5$ and $R^6$ are independently selected from a linear or branched C1-C4 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein $R^5$ and $R^6$ adjacent to one another form a saturated 4- to 7-membered heterocycle with the nitrogen to which they are bound, and wherein the heterocycle optionally contains 1, 2, or 3 heteroatoms selected from N and O; for preparing a compound of formula (F)

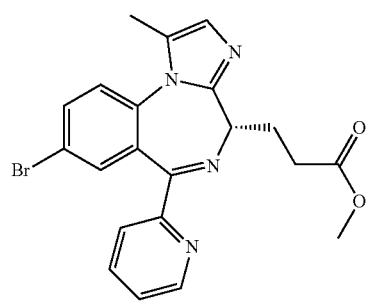

or a pharmaceutically acceptable salt, characterized in that the compound of formula (F) is obtained from compound (DE) by means of the method described in aspects 1 and 2 of the present invention.

In a particular embodiment of the fourth aspect, the present invention relates to the use of the compound of formula (E1)

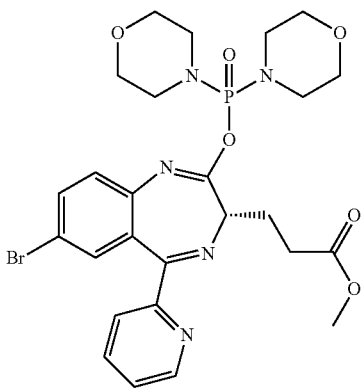

for preparing a compound of formula (F)

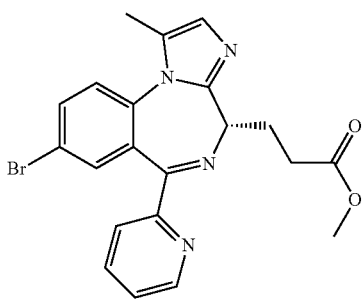

(F)

or a pharmaceutically acceptable salt, characterized in that the compound of formula (F) is obtained from compound (E1) by means of the method described in aspects 1 and 2 of the present invention.

The fifth aspect of the present invention relates to the compound of formula (E),

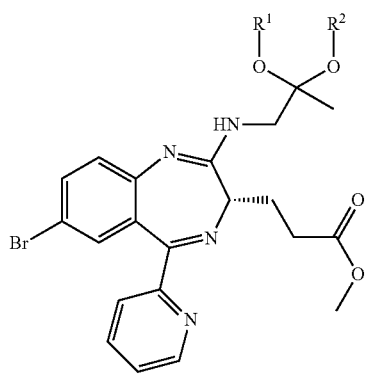

(E)

wherein $R^1$ and $R^2$ are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein $R^1$, together with $R^2$, forms a residue of formula —CH$_2$—(CR$^3$R$^4$)$_n$—CH$_2$—, wherein n is equal to 0, 1, 2, 3, or 4, and wherein $R^3$ and $R^4$ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl.

In a particular embodiment of the fifth aspect, the present invention relates to (3S)-3-[7-bromo-2-(2,2-dimethoxypropylamino)-5-pyridin-2-yl-3H-benzo[e] [1,4]diazepin-3-yl] propionic acid methyl ester of formula (E2)

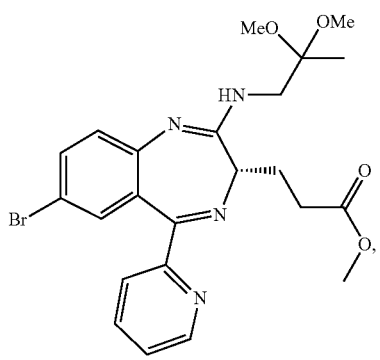

(E2)

DETAILED DESCRIPTION OF THE INVENTION

Figure 1:
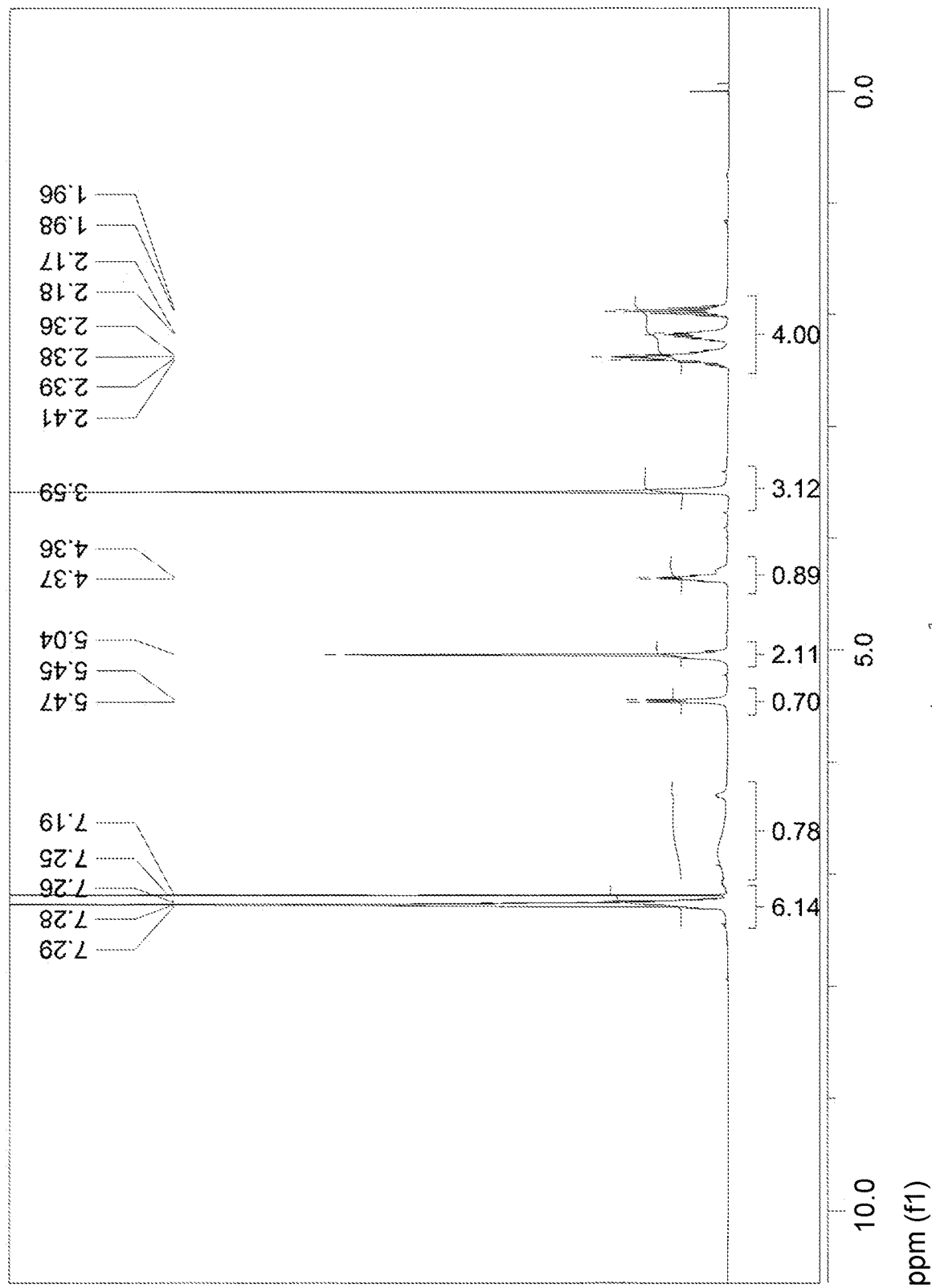
FIG. 1 shows the 1H-NMR of (2S)-2-(benzyloxycarbonylamino)-5-methoxy-5-oxo-pentanoic acid.

The first aspect of the invention defines a method for preparing 3-[(4S)-8-bromo-1-methyl-6-(pyridin-2-yl)-4H-imidazo[1,2-a] [1,4]benzodiazepin-4-yl]-propionic acid methyl ester of formula (F),

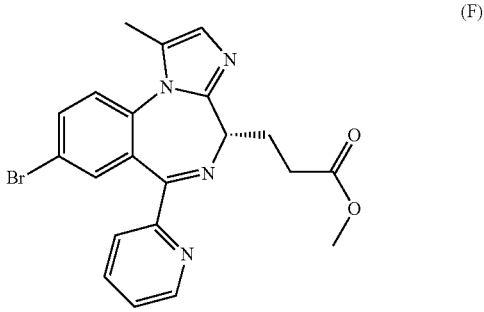 [SMILES: COC(=O)CC[C@@H]1N=C(c2ccccn2)c2cc(Br)ccc2-n2c(C)cnc21]

(F)

or a pharmaceutically acceptable salt, characterized in that it comprises the step of reacting a compound of formula (E),

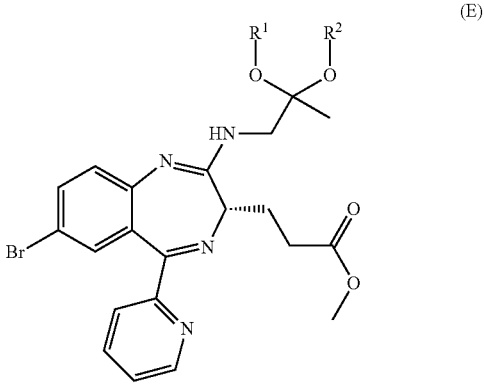

(E)

wherein $R^1$ and $R^2$ are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein $R^1$, together with $R^2$, forms a residue of formula —CH$_2$—(CR$^3$R$^4$)$_n$—CH$_2$—, wherein n is equal to 0, 1, 2, 3, or 4, and wherein $R^3$ and $R^4$ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; with an acid.

In the context of the present invention, where it is defined that a linear or branched alkyl is optionally substituted, it means to define that said linear or branched alkyl is either unsubstituted or is alternatively substituted in one or more positions with at least one group selected from linear or branched C1-C3 alkyl, halogen, amino, alkylamino, or OR', wherein R' represents an H or a linear or branched C1-C6 alkyl. An alkylamino will be understood as —NR"R" wherein each R" is independently selected from H or from linear or branched C1-C3 alkyl.

In a particular embodiment, $R^1$ and $R^2$ are independently selected from an optionally substituted linear or branched C1-C3 alkyl, preferably an unsubstituted linear C1-C3 alkyl. In a preferred embodiment, $R^1$ and $R^2$ are methyl. So in a particular embodiment of the invention, the method for preparing 3-[(4S)-8-bromo-1-methyl-6-(pyridin-2-yl)-4H-imidazo[1,2-a] [1,4]benzodiazepin-4-yl]-propionic acid methyl ester of formula (F),

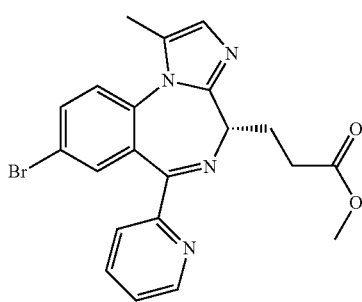

(F)

or a pharmaceutically acceptable salt, is characterized in that it comprises the step of reacting (3S)-3-[7-bromo-2-(2,2-dimethoxypropylamino)-5-pyridin-2-yl-3H-benzo[e] [1,4]diazepin-3-yl]propionic acid methyl ester of formula (E2)

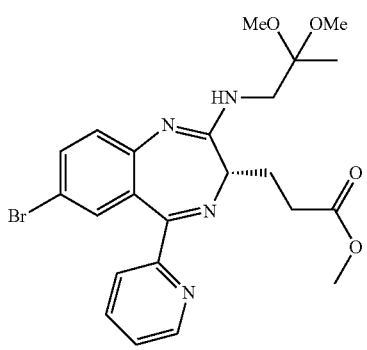

(E2)

with an acid.

The method of the invention has the enormous advantage compared with the state of the art as it does not require an oxidizing agent to convert the intermediate of formula (E1) into the compound of formula (F) or a pharmaceutically acceptable salt, but rather since this occurs via the intermediate acetal of formula (E), the use of an acid is sufficient to lead to cyclization, obtaining the compound of formula (F). This allows improving reaction yield (as demonstrated by the examples) as well as improving process industrialization.

Generally, the acid required for cyclizing the acetal of formula (E) into the compound of formula (F) is an acid typically used in acid hydrolysis reactions, so one skilled in the art will not have any difficulty in identifying which acids can be used in the method of the present invention. An organic acid, or alternatively an inorganic acid, can be selected as an example of acids. Non-limiting examples of the acids that can be used in this step are hydrochloric acid, hydrobromic acid, phosphoric acid, or sulfuric acid, as well as acetic acid, benzoic acid, fumaric acid, oxalic acid, maleic acid, succinic acid, or sulfonic acids, such as ethanedisulfonic acid, methylbenzenesulfonic acid, or benzenesulfonic acid. In a particular embodiment, the acid used for cyclizing the acetal of formula (E) into the compound of formula (F) is a sulfonic acid. Preferably, the acid is selected from ethanedisulfonic acid, methylbenzenesulfonic acid, or benzenesulfonic acid, more preferably benzenesulfonic acid.

The reaction for forming the compound of formula (F) from the acetal of formula (E) is preferably carried out in an organic solvent. In another particular embodiment, the reaction for forming the compound of formula (F) from the acetal of formula (E) is carried out in an anhydrous solvent. Preferably, the compound of formula (F) is obtained from (E) using an acid in an organic solvent.

In a preferred embodiment, the acid used for hydrolyzing acetal (E) is benzenesulfonic acid. In this case, in a one-step synthesis and without having to use more reagents, namely dangerous oxidizers such as Dess-Martin periodinane, the intermediate (E) is converted into the pharmaceutically acceptable besylate salt of 3-[(4S)-8-bromo-1-methyl-6-(pyridin-2-yl)-4H-imidazo[1,2-a] [1,4]benzodiazepin-4-yl]-propionic acid methyl ester of formula (F).

In a particular embodiment, the reaction of (E) with benzenesulfonic acid is carried out in an organic solvent. Preferably, the organic solvent is selected from esters, alcohols, and ketones. More preferably, the organic solvent is selected from methyl acetate, ethyl acetate, isopropyl acetate, methanol, ethanol, n-propanol, isopropanol, acetone, methylisobutylketone, and methylethylketone. Even more preferably, the organic solvent is acetone. The hydrolysis and cyclization reaction is carried out at a temperature not exceeding 90° C., not exceeding 70° C., not exceeding 50° C., not exceeding 40° C. or not exceeding 30° C., preferably not exceeding 20° C.

In a particular embodiment, the hydrolysis and cyclization reaction is carried out under inert atmosphere. Inert atmosphere must be understood as meaning the absence of oxygen.

In another particular embodiment, the compound of formula (E) is reacted with an acid other than benzenesulfonic acid, under conditions identical to those described above. In that context, a pharmaceutically acceptable salt of the compound of formula (F) conjugated depending on the acid used is obtained. Examples of alternative acids are sulfonic acids such as ethanedisulfonic acid or methylbenzenesulfonic acid. In a preferred embodiment, the method of the invention allows obtaining the besylate salt of the compound of formula (F).

In a particular embodiment, for preparing a compound of formula (E), a compound of formula (DE) described above can be used to start and it can be reacted with a primary amine of formula,

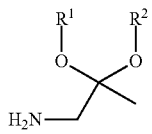

wherein R¹ and R² are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein R¹, together with R², forms a residue of formula —CH₂—(CR³R⁴)ₙ—CH₂—, wherein n is equal to 0, 1, 2, 3, or 4, and wherein R³ and R⁴ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl.

For this reason, a second aspect of the invention contemplates the method for preparing a compound of formula (E),

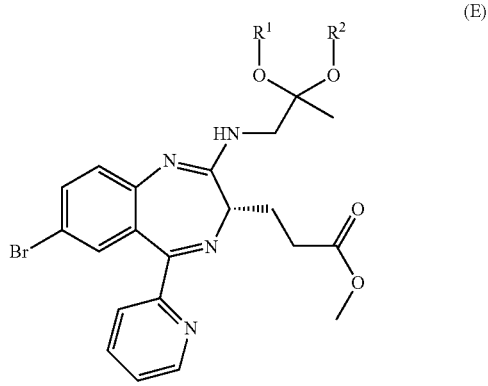

wherein R¹ and R² are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein R¹, together with R², forms a residue of formula —CH₂—(CR³R⁴)ₙ—CH₂—, wherein n is equal to 0, 1, 2, 3, or 4, and wherein R³ and R⁴ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; characterized in that it comprises the step of reacting the compound of formula (DE)

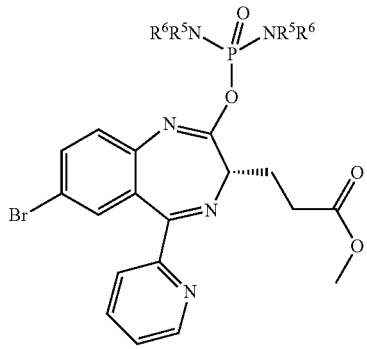

wherein R⁵ and R⁶ are independently selected from a linear or branched C1-C4 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein R⁵ and R⁶ adjacent to one another form a saturated 4- to 7-membered heterocycle with the nitrogen to which they are bound, and wherein the heterocycle optionally contains 1, 2, or 3 heteroatoms selected from N and O;

with said primary amine of formula,

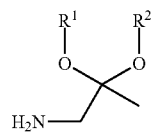

wherein R¹ and R² are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein R¹, together with R², forms a residue of formula —CH₂—(CR³R⁴)ₙ—CH₂—, wherein n is equal to 0, 1, 2, 3, or 4, and wherein R³ and R⁴ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl.

For preparing the compound of formula (E2), the compound of formula (E1) described in WO 2011/032692, for example, can be used to start and be reacted with 2,2-dimethoxy-propylamine. A particular embodiment contemplates the method for preparing (3S)-3-[7-bromo-2-(2,2-dimethoxypropylamino)-5-pyridin-2-yl-3H-benzo[e] [1,4] diazepin-3-yl]propionic acid methyl ester of formula (E2)

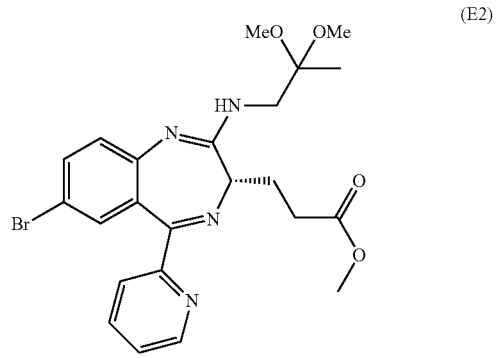 [SMILES: COC(=O)CC[C@@H]1N=C(c2ccccn2)c2cc(Br)ccc2N=C1NCC(C)(OC)OC]

characterized in that it comprises the step of reacting the compound of formula (E1)

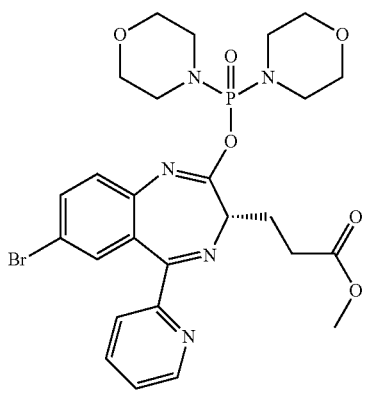

(E1)

with 2,2-dimethoxy-propylamine.

In a particular embodiment, the reaction for obtaining the compound of formula (E) from the compound of formula (DE) is carried out under anhydrous conditions. In another particular embodiment, said reaction is carried out in an anhydrous organic solvent. The anhydrous organic solvent is preferably selected from cyclic ethers, particularly tetrahydrofuran or 2-methyltetrahydrofuran, preferably tetrahydrofuran. The reaction for forming the acetal is carried out at a temperature not exceeding 90° C., not exceeding 70° C., not exceeding 50° C., not exceeding 40° C. or not exceeding 30° C., preferably not exceeding 20° C.

It is therefore obvious from the present disclosure that the acetal of formula (E) is an intermediate of high commercial interest since it allows obtaining the compound of formula (F), or a pharmaceutically acceptable salt thereof, in a single synthesis step and without demanding complicated reaction conditions, such as the use of dangerous oxidizers. Based on the foregoing, a third aspect of the invention contemplates the use of the compound of formula (E),

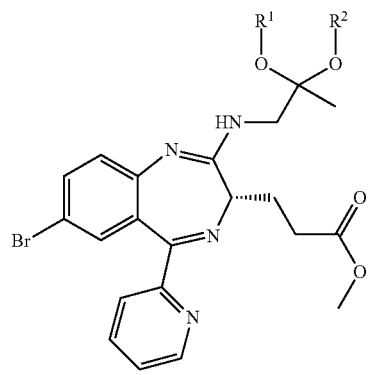

(E)

wherein $R^1$ and $R^2$ are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein $R^1$, together with $R^2$, forms a residue of formula —$CH_2$—$(CR^3R^4)_n$—$CH_2$—, wherein n is equal to 0, 1, 2, 3, or 4, and wherein $R^3$ and $R^4$ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl;

for preparing a compound of formula (F)

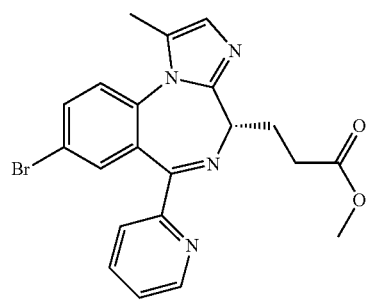

(F)

or a pharmaceutically acceptable salt.

A particular embodiment contemplates the use of (3S)-3-[7-bromo-2-(2,2-dimethoxypropylamino)-5-pyridin-2-yl-3H-benzo[e] [1,4]diazepin-3-yl]propionic acid methyl ester of formula (E2)

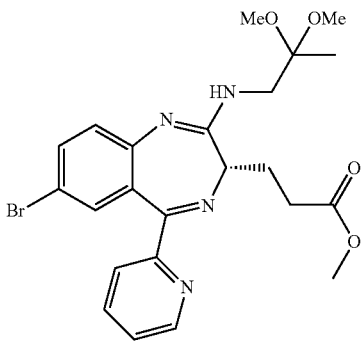

(E2)

for preparing a compound of formula (F)

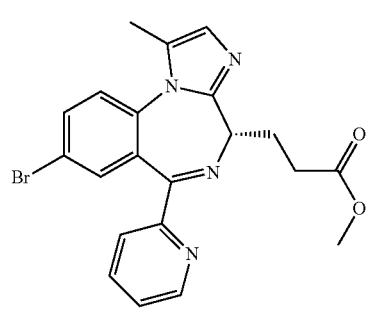

(F)

or a pharmaceutically acceptable salt.

Alternatively, a fourth aspect of the invention also contemplates the use of the compound of formula (DE)

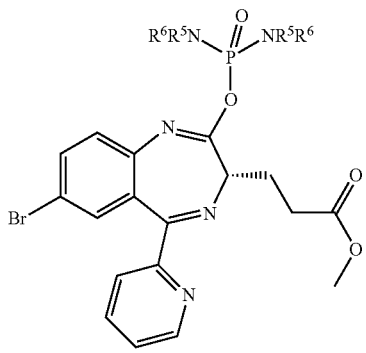

(DE)

wherein $R^5$ and $R^6$ are independently selected from a linear or branched C1-C4 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein $R^5$ and $R^6$ adjacent to one another form a saturated 4- to 7-membered heterocycle with the nitrogen to which they are bound, and wherein the heterocycle optionally contains 1, 2, or 3 heteroatoms selected from N and O; for preparing a compound of formula (F)

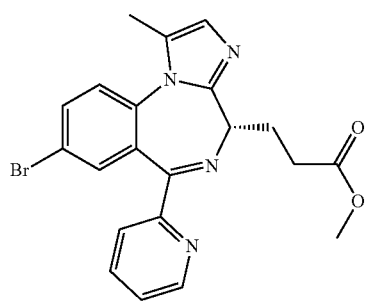

(F)

or a pharmaceutically acceptable salt, characterized in that the compound of formula (F) is obtained from compound (DE) by means of the method described in the present invention.

A preferred embodiment contemplates the use of the compound of formula (DE)

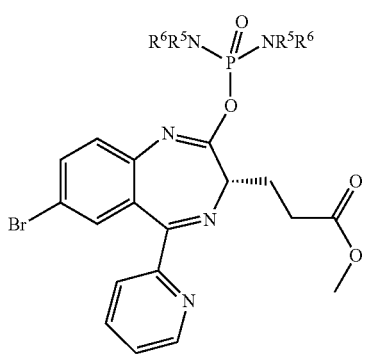

(DE)

wherein $R^5$ and $R^6$ are independently selected from a linear or branched C1-C4 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein $R^5$ and $R^6$ adjacent to one another form a saturated 4- to 7-membered heterocycle with the nitrogen to which they are bound, and wherein the heterocycle optionally contains 1, 2, or 3 heteroatoms selected from N and O; for preparing a compound of formula (F)

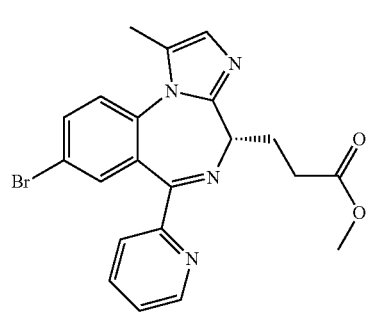

(F)

or a pharmaceutically acceptable salt, characterized in that the compound of formula (F) is obtained from compound (DE) by means of the method of the present invention, using 2,2-dimethoxy-propylamine via the intermediate of formula (E2).

A particular embodiment contemplates the use of the compound of formula (E1)

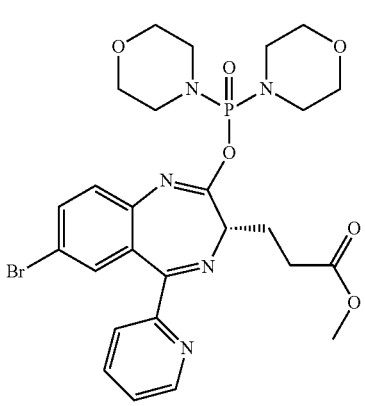

(E1)

for preparing a compound of formula (F)

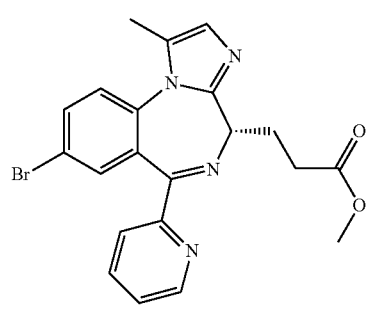

(F)

or a pharmaceutically acceptable salt, characterized in that the compound of formula (F) is obtained from compound (E1) by means of the method of the present invention. In an even more preferred embodiment, the method uses 2,2-dimethoxy-propylamine so it occurs via the intermediate of formula (E2).

The acetal of formula (E) obtainable by means of the reaction of (DE) with a primary amine of formula,

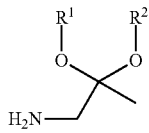

wherein $R^1$ and $R^2$ are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein $R^1$, together with $R^2$, forms a residue of formula —CH$_2$—(CR$^3$R$^4$)$_n$—CH$_2$—, wherein n is equal to 0, 1, 2, 3, or 4, and wherein $R^3$ and $R^4$ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl;
is a novel compound. Therefore, the final aspect of the invention relates to the compound of formula (E)

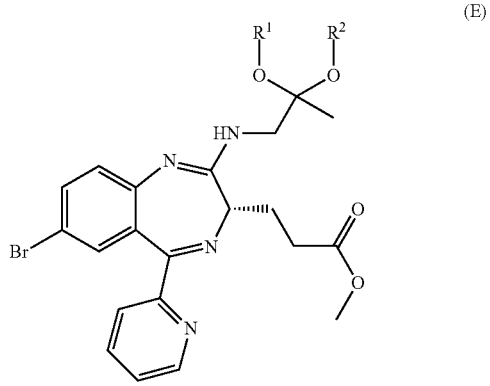

(E)

wherein $R^1$ and $R^2$ are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein $R^1$, together with $R^2$, forms a residue of formula —CH$_2$—(CR$^3$R$^4$)$_n$—CH$_2$—, wherein n is equal to 0, 1, 2, 3, or 4, and wherein $R^3$ and $R^4$ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl.

In a particular embodiment, $R^1$ and $R^2$ are independently selected from an unsubstituted linear or branched C1-C6 alkyl; or $R^1$, together with $R^2$, forms a residue of formula —CH$_2$—(CR$^3$R$^4$)$_n$—CH$_2$—, wherein n is equal to 0, 1, 2, or 3, and wherein $R^3$ and $R^4$ are independently selected from a hydrogen or an unsubstituted linear or branched C1-C6 alkyl.

In a particular embodiment, $R^1$ and $R^2$ are independently selected from an unsubstituted linear or branched C1-C3 alkyl. In another particular embodiment, $R^1$, together with $R^2$, forms a residue of formula —CH$_2$—(CR$^3$R$^4$)$_n$—CH$_2$—, wherein n is equal to 0. In another particular embodiment, $R^1$, together with $R^2$, forms a residue of formula —CH$_2$—(CR$^3$R$^4$)$_n$—CH$_2$—, wherein n is 1, 2, 3, or 4.

Additionally, the acetal of formula (E2) obtainable by means of the reaction of (E1) with 2,2-dimethoxypropylamine is a novel compound. Therefore, a preferred embodiment of the invention relates to the (3S)-3-[7-bromo-2-(2,2-dimethoxypropylamino)-5-pyridin-2-yl-3H-benzo[e] [1,4]diazepin-3-yl]propionic acid methyl ester compound of formula (E2)

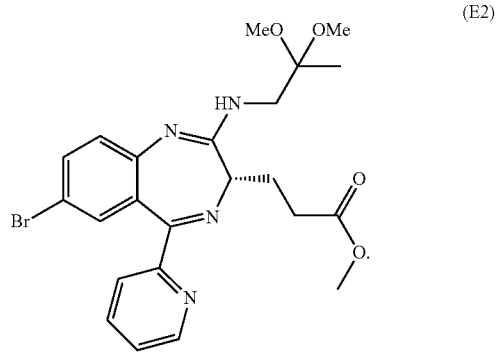 [SMILES: COC(=O)CC[C@@H]1N=C(c2ccccn2)c2cc(Br)ccc2N=C1NCC(C)(OC)OC]

(E2)

As described above, preparing the compound of formula (E) may start from a compound of formula (DE)

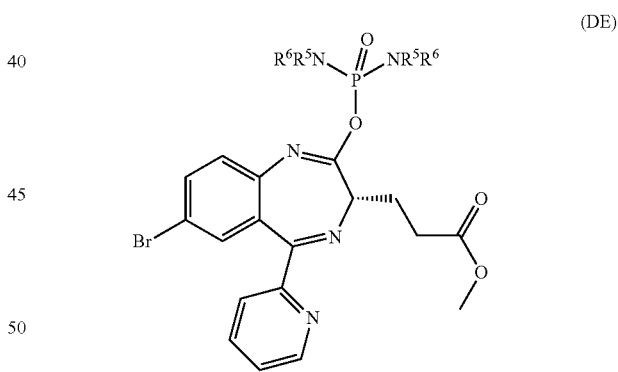

(DE)

wherein $R^5$ and $R^6$ are independently selected from a linear or branched C1-C4 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein $R^5$ and $R^6$ adjacent to one another form a saturated 4- to 7-membered heterocycle with the nitrogen to which they are bound, and wherein the heterocycle optionally contains 1, 2, or 3 heteroatoms selected from N and O.

A compound of formula (DE) may in turn be obtained from 3-[(3S)-7-bromo-2-oxo-5-(pyridin-2-yl)-2,3-dihydro-1H-[1,4]-benzodiazepin-3-yl] propionic acid methyl ester of formula (D)

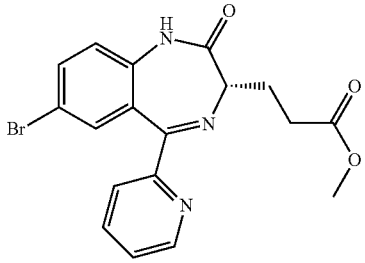

(D)

by activating with lithium diisopropylamide and reacting with a phosphoryl chloride of general formula

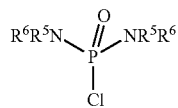

wherein $R^5$ and $R^6$ are independently selected from a linear or branched C1-C4 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein $R^5$ and $R^6$ adjacent to one another form a saturated 4- to 7-membered heterocycle with the nitrogen to which they are bound, and wherein the heterocycle optionally contains 1, 2, or 3 heteroatoms selected from N and O.

In a particular embodiment, and as described above, preparing the compound of formula (E2) may start from the compound of formula (E1). Compound (E1) may in turn be obtained from 3-[(3S)-7-bromo-2-oxo-5-(pyridin-2-yl)-2,3-dihydro-1H-[1,4]-benzodiazepin-3-yl] propionic acid methyl ester of formula (D)

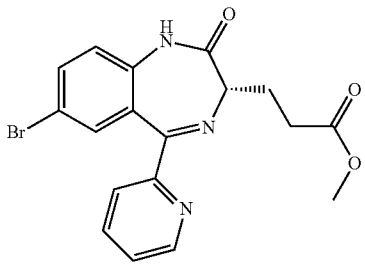

(D)

by activating with lithium diisopropylamide and reacting with bis-morpholinophosphorylchloride (BMPC, Ning et al., J Org. Chem. 1976, 41, 2720-2724; Ning et al., J Org. Chem. 1976, 41, 2724-2727). This reaction is described, for example, in WO 2011/032692, wherein lactam of formula (D) is reacted with lithium diisopropylamide (LDA) and bis-morpholinophosphorylchloride (BMPC) to yield 3-[(3S)-7-bromo-2-(bis-morpholinophosphoryloxy)-5-(pyridin-2-yl)-[1,4]-benzodiazepin-3-yl]-propionic acid methyl ester of formula (E1),

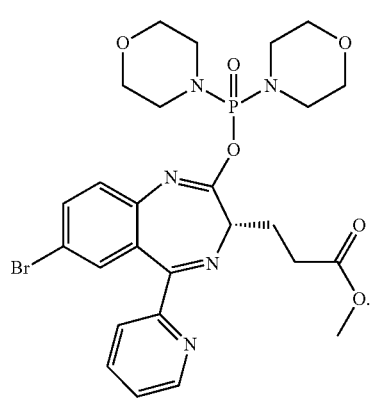

(E1)

3-[(3S)-7-bromo-2-oxo-5-(pyridin-2-yl)-2,3-dihydro-1H-[1,4]-benzodiazepin-3-yl] propionic acid methyl ester of formula (D) can be prepared by reacting methyl (4S)-4-amino-5-[4-bromo-2-(pyridine-2-carbonyl)aniline]-5-oxo-pentanoate hydrobromide salt of formula (I-C)

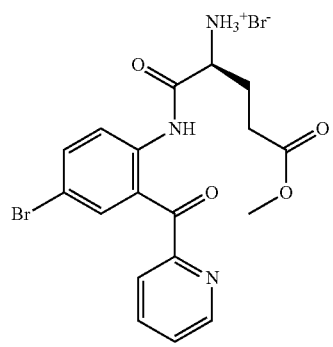

(I-C)

with a base.

Throughout this specification and in the attached claims, the term "base" is used to describe any substance capable of accepting protons increasing the pH of a solution. In an aqueous medium, said substance provides OH⁻ ions to said medium. The strength of a base can be measured through the pKb constant, with the base being stronger the lower its pKb is.

Therefore, the conversion of the compound of formula (I-C) into the compound of formula (D) is performed in the presence of a base. It is preferable for the base used to convert compound (I-C) into compound (D) to be a base with a pKb less than 8.0. Suitable non-limiting examples of bases that could be used are alkaline hydroxides such as NaOH or KOH, carbonic acid salts such as sodium bicarbonate or potassium bicarbonate or also non-nucleophilic amines such as triethylamine ($Et_3N$) or N,N-diisopropylethylamine (DIPEA). Preferably, the base used is sodium bicarbonate.

The reaction for forming the compound of formula (D) from the compound of formula (I-C) can generally be carried out in an aqueous medium with a pH value comprised between 3 and 8, preferably between 3 and 5, more preferably between 3.5 and 4.5, even more preferably with a pH value comprised between 3.8 and 4.

The solvents in which the reaction for converting (I-C) into (D) can be carried out are selected from water and alcohols and mixtures thereof, preferably from water, methanol, ethanol, propanol, isopropanol, and butanol, and more preferably water.

In relation to the reaction temperature, the reaction for converting (I-C) into (D) can be carried out at a temperature comprised between 0° C. and 40° C., preferably between 20° C. and 30° C., and more preferably between 20 and 23° C. The reaction for converting (I-C) into (D) is generally preferred to be carried out using water as a solvent and at a temperature comprised between 20 and 30° C.

As an example, the reaction for converting (I-C) into (D) starts by subjecting the compound of formula (I-C) to the pH values described above, and the reaction is considered finished in less than 1 hour, preferably in less than 30 minutes, more preferably in less than 15 minutes, even more preferably in less than 5 minutes.

The compound of formula (D) is soluble at least in alkyl esters, toluene, methyltetrahydrofuran, and dichloromethane. Therefore, after reaching the pH values described above, for example, by means of adding a base to an acidic aqueous solution of the compound of formula (I-C), the compound of formula (D) can be isolated by adding dichloromethane to said acidic aqueous solution (liquid-liquid extraction). Evaporation of dichloromethane produces the compound of formula (D) in solid state.

In a particular embodiment, the solid of the compound of formula (D) obtained according to the preceding paragraph can be purified by means of recrystallization, preferably by means of recrystallization using a solvent in which the compound (D) has high solubility, preferably a solubility not less than 1 g/L, and by adding an antisolvent, i.e., a solvent in which the compound (D) has low solubility, preferably a solubility not greater than or equal to 1 g/L. Ketones and alcohols, preferably acetone and isopropanol, are preferred solvents. Preferably, the compound of formula (D) is dissolved in isopropanol and the latter is heated at the reflux temperature. Alkanes and ethers, preferably n-heptane or methyl-tert-butylether, are preferred antisolvents. N-heptane is preferably selected as an antisolvent for recrystallizing the compound of formula (D). The purity of the compound of formula (D) can generally be determined by means of nuclear magnetic resonance (NMR) or by means of liquid chromatography.

In a preferred embodiment, the compound of formula (I-C) is prepared by means of reacting methyl (4S)-4-(benzyloxycarbonylamino)-5-[4-bromo-2-(pyridine-2-carbonyl)aniline]-5-oxo-pentanoate of formula (I-B)

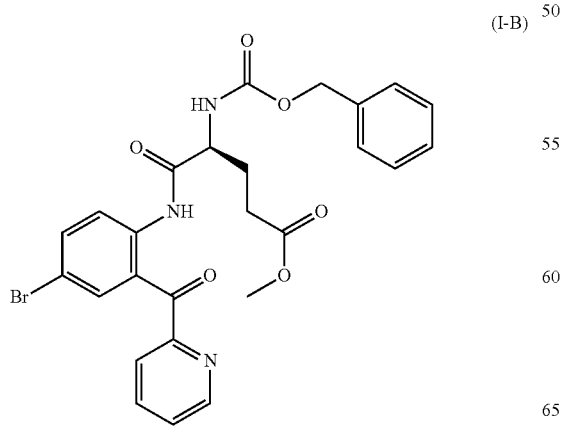

(I-B)

with hydrobromic acid.

The intermediate of formula (I-B) can be dissolved in glacial acetic acid at a low temperature, such as between 10 and 20° C., for example, preferably between 10 and 12° C. Hydrobromic acid (HBr) may be added to this acidic solution so as to deprotect the amine by means of the CBz group leaving and thereby obtain the compound of formula (I-C).

In a particular embodiment, the intermediate of formula (I-B) can be dissolved in acetic acid, dichloromethane, toluene, or methyl-tert-butylether, preferably in glacial acetic acid. In another particular embodiment, the intermediate of formula (I-B) can be dissolved in any of the mentioned solvents at a temperature of 10° C. to 20° C., preferably 10° C. to 12° C.

In a particular embodiment, the reaction for forming the compound of formula (I-C) from the compound of formula (I-B) is carried out by means of slowly adding HBr dissolved in glacial acetic acid, to a solution of (I-B) previously dissolved in acetic acid as described above, at a temperature comprised between 10 and 20° C. Once the addition of HBr has ended, in a particular embodiment the temperature is left to go up to between 15 and 25° C., preferably up to 20° C. In a particular embodiment, the resulting acidic solution is left to stir for 1 to 3 hours, preferably for 2 hours.

In a particular embodiment, the compound of formula (I-C) thus formed is not isolated and the resulting acidic medium is directly neutralized until reaching the pH values mentioned above. In a particular embodiment, said resulting acidic medium can be neutralized by means of adding sodium bicarbonate to the acidic aqueous solution of the compound of formula (I-C). Said neutralization is the neutralization of the acidic medium mentioned above, which gives rise to the reaction for converting the compound of formula (I-C) into the compound of formula (D).

Alternatively, the compound of formula (I-C) can be isolated by treating corresponding reaction mass with a suitable organic solvent, preferably an alkyl acetate, more preferably isopropyl acetate, in order to obtain a solid that is filtered.

In another preferred embodiment, methyl (4S)-4-(benzyloxycarbonylamino)-5-[4-bromo-2-(pyridine-2-carbonyl)aniline]-5-oxo-pentanoate of formula (I-B) is prepared by means of reacting the compound of formula (A)

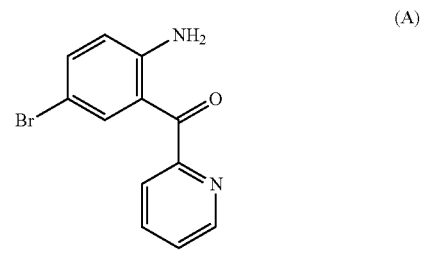 [SMILES: Nc1ccc(Br)cc1C(=O)c1ccccn1]

(A)

with (2S)-2-(benzyloxycarbonylamino)-5-methoxy-5-oxo-pentanoic acid in the presence of a coupling agent. Compound (2-amino-5-bromo-phenyl)-pyridin-2-yl-methanone of formula (A) is known from the state of the art, with the preparation thereof being described, for example, in the publication by Leganza A. et al., *European Journal of Organic Chemistry*, 2006, 13, 2987-2990, and it may also be identified according to its CAS number: 1563-56-0.

(2S)-2-(benzyloxycarbonylamino)-5-methoxy-5-oxo-pentanoic acid can be represented according to the following structural formula,

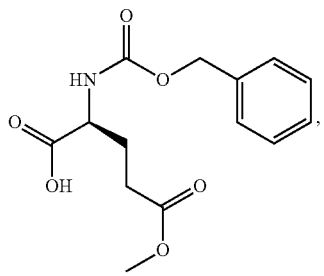 [SMILES: COC(=O)CC[C@H](NC(=O)OCc1ccccc1)C(=O)O]

and can be obtained by means of the method described in Example 1 by protecting (2S)-2-amino-5-methoxy-5-oxo-pentanoic acid with benzyl chloroformate.

One skilled in the art will recognize what is to be understood by coupling agent in the present context in reference to an amino acid coupling agent. An example of a coupling agent capable of facilitating the formation of amide groups by reaction between an $NH_2$ group and a COOH group is N,N'-dicyclohexylcarbodiimide (DCC).

In a preferred embodiment, the coupling reaction between the compound of formula (A) and (2S)-2-(benzyloxycarbonylamino)-5-methoxy-5-oxo-pentanoic acid is carried out in dichloromethane in the presence of a coupling agent. In another preferred embodiment, the coupling reaction between the compound of formula (A) and (2S)-2-(benzyloxycarbonylamino)-5-methoxy-5-oxo-pentanoic acid is carried out in dichloromethane in the presence of a coupling agent and at a temperature comprised between −10° C. and 15° C. In yet another preferred embodiment, the addition of the coupling agent is done at a temperature less than zero degrees centigrade, preferably at −10° C., and once the addition has ended, the reaction temperature is maintained. In another preferred embodiment, the coupling agent is DCC. Preferably, the reaction for forming the compound of formula (I-B) is carried out by means of stirring for 1 to 3 days, more preferably for 48 hours. The reaction product can be purified by means of filtration and recrystallization. As solvents useful for recrystallizing the compound of formula (I-B), there are alcohols, alkyl esters, ketones, methyl-tert-butylether or toluene, preferably methyl-tert-butylether.

The present application also describes the method for synthesizing the compound of formula (D), via the intermediates of formula (I-B) and (I-C), having a yield that is significantly greater than what is produced by means of the methods described in WO 2011/032692 or in WO 00/69836. This will become obvious throughout the present disclosure, particularly as a result of the examples. In turn, the compound of formula (D) thus obtained can be used for the synthesis of 3-[(4S)-8-bromo-1-methyl-6-(pyridin-2-yl)-4H-imidazo[1,2-a] [1,4]benzodiazepin-4-yl]-propionic acid methyl ester of formula (F), as inferred from the examples and the claims.

Therefore, a particular embodiment of the present invention relates to the method for the preparation of a compound of formula (F) according to the method described above, characterized in that the compound of formula (D) is obtained from the compound of formula (I-C).

In another particular embodiment, the present invention relates to a method for the preparation of a compound of formula (F) according to the method described above, characterized in that the compound of formula (D) is obtained from the compound of formula (I-C) according to the method of the invention, and in turn characterized in that the compound of formula (I-C) is obtained by reacting the compound of formula (I-B) with hydrobromic acid.

Another particular embodiment of the present invention relates to the method for the preparation of a compound of formula (F) according to the method described above, characterized in that the compound of formula (D) is obtained from the compound of formula (I-C) according to the method of the invention, characterized in that the compound of formula (I-C) is obtained by reacting the compound of formula (I-B) with hydrobromic acid, and in turn characterized in that the compound of formula (I-B) is obtained by reacting the compound of formula (A) with (2S)-2-(benzyloxycarbonylamino)-5-methoxy-5-oxo-pentanoic acid in the presence of a coupling agent.

The compounds of formula (I-C) and formula (I-B) are intermediates useful in the synthesis of the compound of formula (F). Therefore, the present invention relates to the use of methyl (4S)-4-amino-5-[4-bromo-2-(pyridine-2-carbonyl)aniline]-5-oxo-pentanoate hydrobromide salt of formula (I-C) for preparing a compound of formula (F). In a particular embodiment, said use is carried out by means of the method of the invention.

The present invention also relates to the use of methyl (4S)-4-(benzyloxycarbonylamino)-5-[4-bromo-2-(pyridine-2-carbonyl)aniline]-5-oxo-pentanoate of formula (I-B) for preparing a compound of formula (F). In a particular embodiment, said use is carried out by means of the method of the invention.

In addition to the compound of formula (E2) described above, the present invention also relates to the compound methyl (4S)-4-(benzyloxycarbonylamino)-5-[4-bromo-2-(pyridine-2-carbonyl)aniline]-5-oxo-pentanoate of formula (I-B)

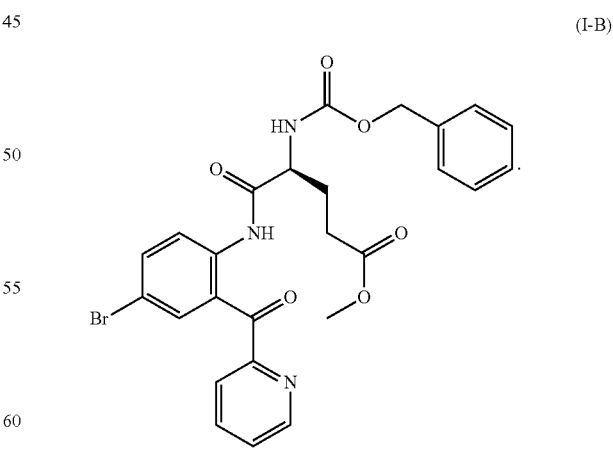

Additionally, the present invention relates to the compound methyl (4S)-4-amino-5-[4-bromo-2-(pyridine-2-carbonyl)aniline]-5-oxo-pentanoate hydrobromide salt of formula (I-C)

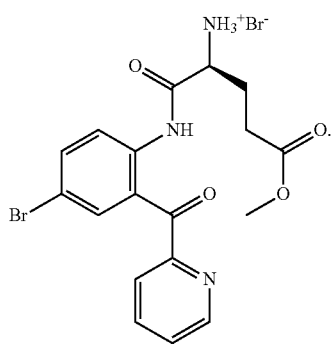

(I-C)

Example 1. Obtaining (2S)-2-(benzyloxycarbonylamino)-5-methoxy-5-oxo-pentanoic acid 22.4 g (139 mmol) of (2S)-2-amino-5-methoxy-5-oxopentanoic acid (Glu(OMe)—OH) were mixed with 420 mL of dichloromethane. The mixture was cooled at 0° C. and 30.2 g (278 mmol) of trimethylsilyl chloride were added, keeping the temperature between 0 and 5° C. 45.3 g (350 mmol) of N,N-diisopropylethylamine were then slowly added, keeping the temperature between 0 and 5° C. The resulting mixture was heated to the reflux temperature and kept under stirring for 1 hour and 30 minutes. The reaction mixture was cooled at a temperature of 0° C. and 20 mL (23.9 g, 140 mmol) of benzyl chloroformate were added at a temperature between 0 and 5° C. The resulting reaction mixture was kept at the indicated temperature for 30 minutes, and then for 2 hours at a temperature of about 25° C.

The reaction mixture was concentrated with a vacuum and 295 mL of an 8% aqueous sodium bicarbonate solution and 280 mL of isopropyl acetate were added. The aqueous phase was separated by means of decantation, and it was acidified to a pH of about 2 by means of a 37% aqueous HCl solution. The resulting aqueous phase was extracted with isopropyl acetate (3×100 mL). The solvent from the pooled organic phases was distilled by means of a vacuum until obtaining 40.7 g (99.0%) of a white solid with a purity greater than 99.0% corresponding to (2S)-2-(benzyloxycarbonylamino)-5-methoxy-5-oxo-pentanoic acid (Cbz-Glu(OMe)—OH). The purity of the obtained products was analyzed by means of the ultra high performance liquid chromatography technique in Waters Acquity HClass equipment, equipped with a variable wave detector and temperature-controlled oven for the column. FIG. 1 shows the 1H-NMR spectrum. 1H-NMR (CDCl₃, 400 MHz) δ(ppm): 7.26 (5H, m), 5.47 (1H, d), 5.04 (2H, s), 4.37 (1H, m), 3.59 (3H, s), 2.3 (2H, m), 2.18 (1H, m) 1.96 (1H, m).

Example 2. Obtaining methyl (4S)-4-(benzyloxycarbonylamino)-5-[4-bromo-2-(pyridine-2-carbonyl) aniline]-5-oxo-pentanoate (I-B)

38.6 g (139 mmol) of (2-amino-5-bromophenyl)-pyridin-2-yl-methanone of formula (A) and 45.2 g (153 mmol) of (2S)-2-(benzyloxycarbonylamino)-5-methoxy-5-oxo-pentanoic acid were dissolved in 200 mL of dichloromethane at a temperature of about 15° C. The solution was cooled at −10° C., and a previously prepared solution containing 32.2 g (156 mmol) of N,N'-dicyclohexylcarbodiimide in 65 mL of dichloromethane was slowly added at said temperature. The reaction mixture was kept under stirring at a temperature of about −10° C. for 48 hours, and the salts resulting from the reaction were then filtered at a temperature of about 15° C.

Figure 2:
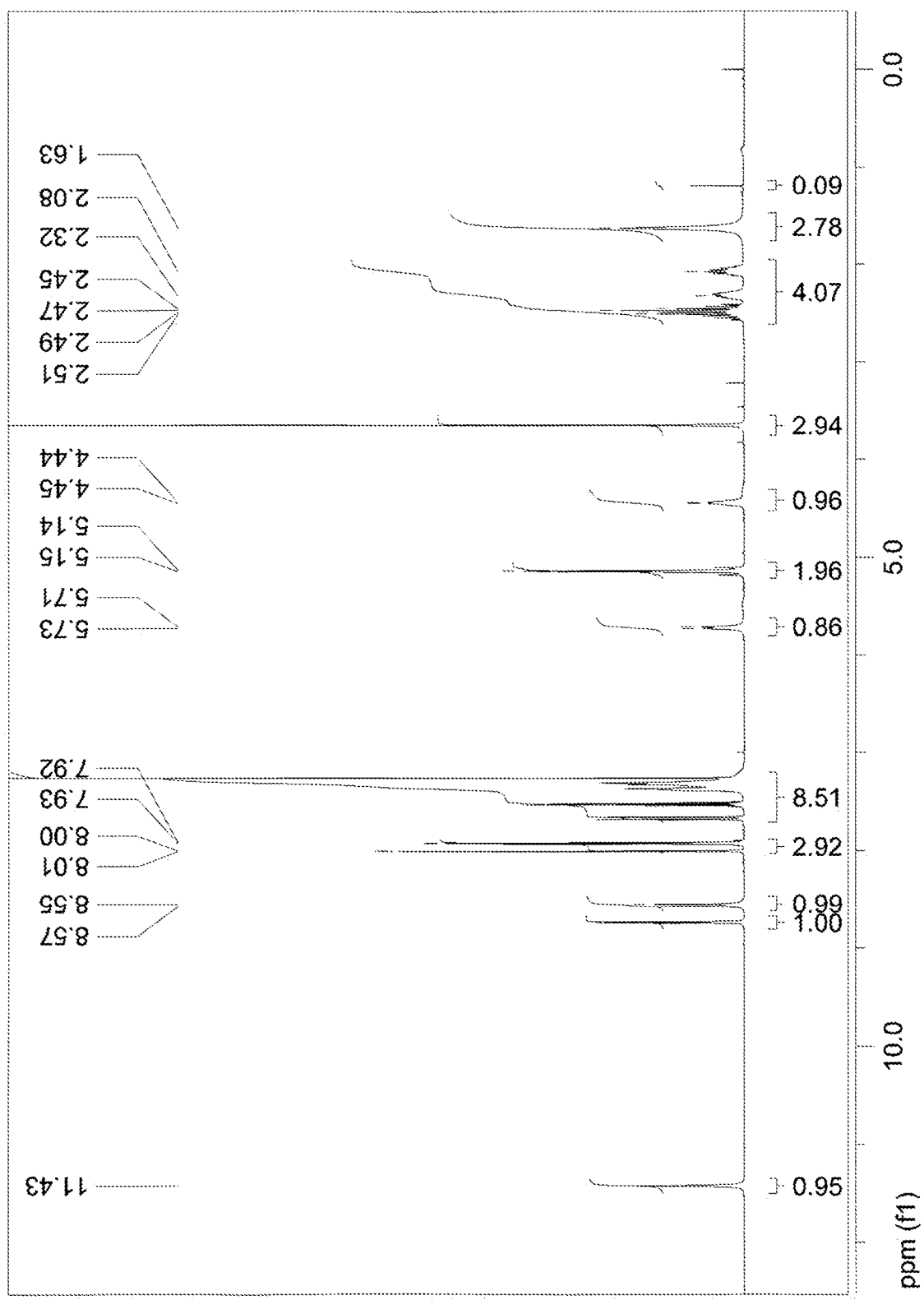
FIG. 2 shows the 1H-NMR of the compound of formula (I-B).

The reaction solvent was removed by means of distillation with a vacuum at the maximum temperature of 25° C., and 250 mL of methyl-tert-butylether were added. The obtained mixture was heated at 50° C. and then slowly cooled at a temperature of about 25° C. The resulting solid was filtered and oven-dried at 50° C. 72.3 g (93.6%) of a very slightly yellowish solid corresponding to methyl (4S)-4-(benzyloxycarbonylamino)-5-[4-bromo-2-(pyridine-2-carbonyl)aniline]-5-oxo-pentanoate of formula (I-B) were thereby obtained. The purity of the obtained products was analyzed by means of the ultra high performance liquid chromatography technique in Waters Acquity HClass equipment, equipped with a variable wave detector and temperature-controlled oven for the column. FIG. 2 shows the 1H-NMR spectrum. 1H-NMR (CDCl₃, 400 MHz) δ(ppm): 11.43 (1H, s), 8.73 (1H, d), 8.56 (1H, d), 8 (1H, d), 7.93 (1H, s), 7.92 (1H, s), 7.67 (1H, dd), 7.52 (1H, m), 7.35 (5H, m), 5.71 (1H, d), 5.04 (2H, m), 4.45 (1H, m), 3.65 (3H, s), 2.50 (2H, m), 2.31 (1H, m), 2.07 (1H, m)

Example 3. Obtaining 3-[(3S)-7-bromo-2-oxo-5-(pyridin-2-yl)-2,3-dihydro-1H-[1,4]-benzodiazepin-3-yl] Propionic Acid Methyl Ester of Formula (D)

35.0 g (63 mmol) of methyl (4S)-4-(benzyloxycarbonylamino)-5-[4-bromo-2-(pyridine-2-carbonyl)aniline]-5-oxo-pentanoate of formula (I-B) were dissolved in 70 mL of glacial acetic acid. 45.7 mL (61.9 g, 253 mmol) of a previously prepared 33% by weight solution of HBr in glacial acetic acid were added slowly, keeping the temperature between 10 and 12° C. Once the addition ended, the temperature of the mixture obtained was left to go up to about 20° C., and it was kept under stirring for 2 hours between 15 and 20° C.

Figure 3:
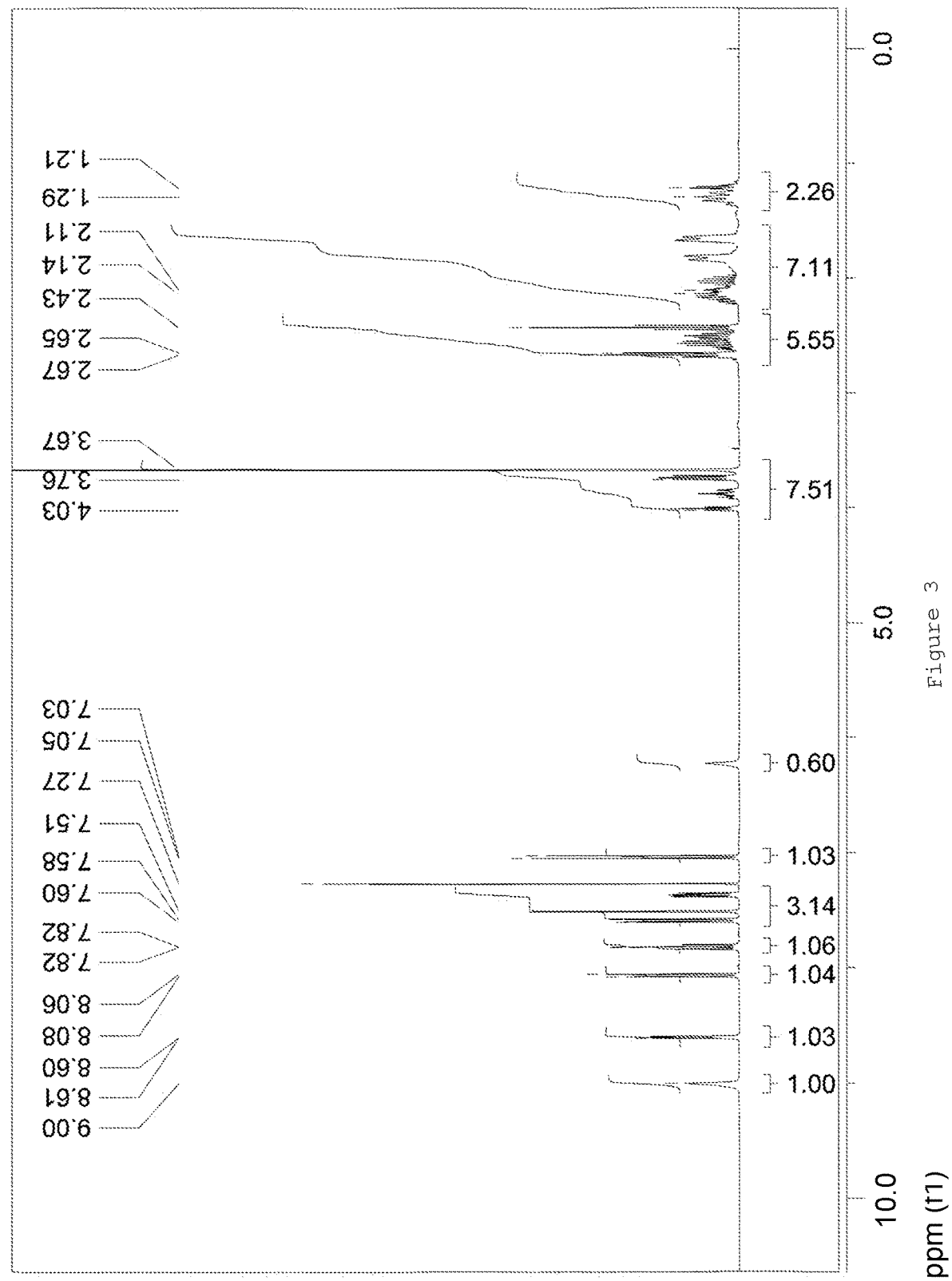
FIG. 3 shows the 1H-NMR of the compound of formula (D).

Once it no longer had to be kept under the aforementioned conditions, 120 mL of water and 50 mL of dichloromethane were added. The resulting aqueous phase containing methyl (4S)-4-amino-5-[4-bromo-2-(pyridine-2-carbonyl)aniline]-5-oxo-pentanoate hydrobromide salt of formula (I-C) was separated, and the pH thereof was adjusted to the range of 3.8-4 by means of adding sodium bicarbonate at a temperature of about 25° C. Dichloromethane was added, and the organic phase containing the reaction product corresponding to 3-[(3S)-7-bromo-2-oxo-5-(pyridin-2-yl)-2,3-dihydro-1H-[1,4]-benzodiazepin-3-yl] propionic acid methyl ester of formula (D) was separated. The organic solvent was vacuum-distilled, and 50 mL of isopropanol were added to the resulting residue. The obtained mixture was heated at the reflux temperature (about 82° C.), and 50 mL of n-heptane were then added. The mixture was cooled slowly to about 20° C., and the resulting solid was filtered and oven-dried, finally obtaining 22.4 g (88.2%) of 3-[(3S)-7-bromo-2-oxo-5-(pyridin-2-yl)-2,3-dihydro-1H-[1,4]-benzodiazepin-3-yl] propionic acid methyl ester of formula (D) with a purity of 99.0%. The purity of the obtained products was analyzed by means of the ultra high performance liquid chromatography technique in Waters Acquity HClass equipment, equipped with a variable wave detector and temperature-controlled oven for the column. FIG. 3 shows the 1H-NMR spectrum. 1H-NMR (CDCl₃, 400 MHz) δ(ppm): 9.01 (1H, s), 8.59 (1H, m), 8.05 (1H, d), 7.81 (1H, m), 7.58 (1H, m), 7.5 (1H, d), 7.36 (1H, m), 7.02 (1H, d), 3.74 (1H, m), 3.67 (3H, s), 2.67 (2H, m), 2.50 (2H, m).

Example 4. Obtaining methyl (4S)-4-amino-5-[4-bromo-2-(pyridine-2-carbonyl)aniline]-5-oxo-pentanoate Hydrobromide Salt of Formula (I-C)

Figure 4:
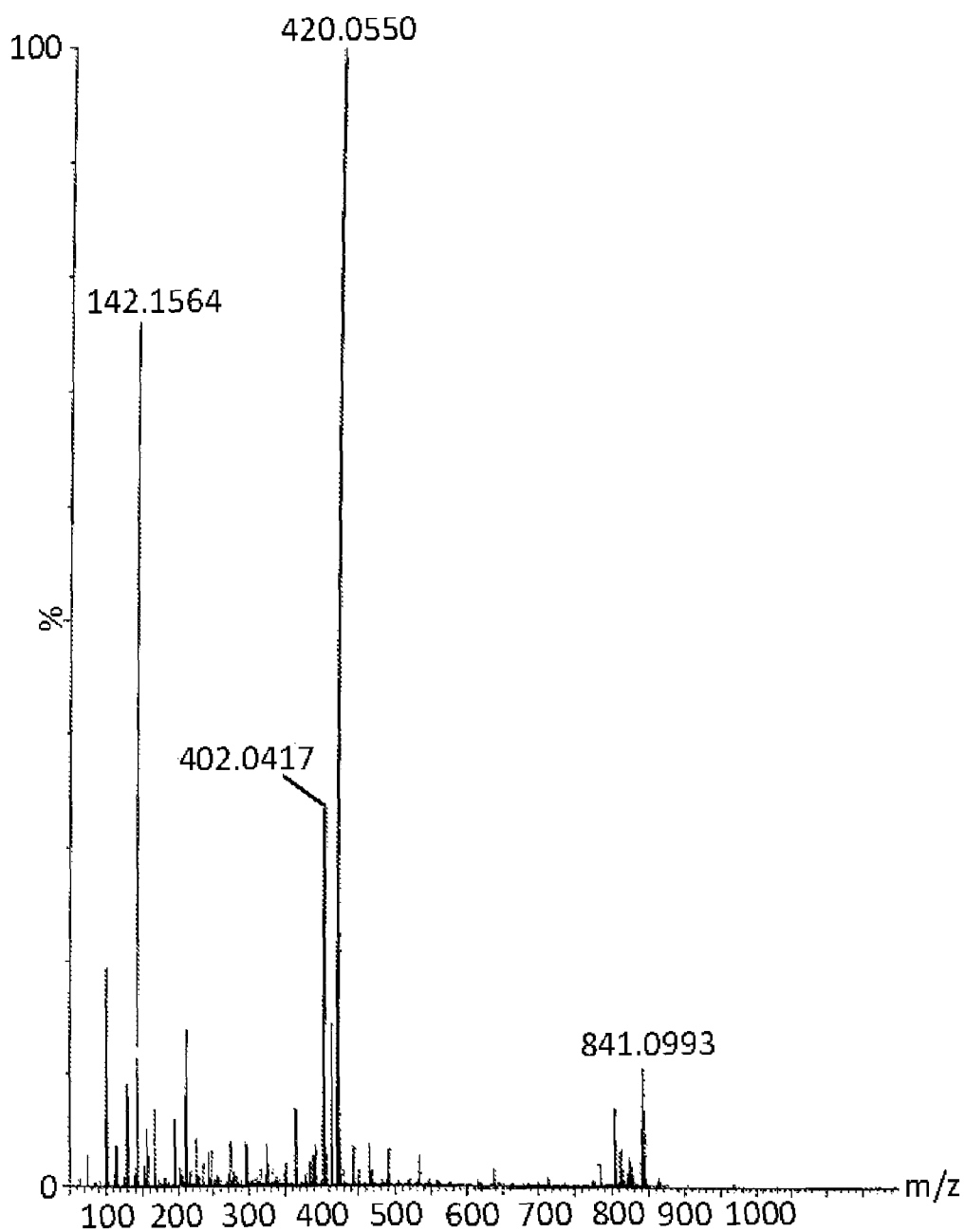
FIG. 4 shows the mass spectrometry of the compound of formula (I-C).

35.0 g (63 mmol) of methyl (4S)-4-(benzyloxycarbonylamino)-5-[4-bromo-2-(pyridine-2-carbonyl)aniline]-5-oxo-pentanoate of formula (I-B) were dissolved in 70 mL of glacial acetic acid. 45.7 mL (61.9 g, 253 mmol) of a previously prepared 33% by weight solution of HBr in glacial acetic acid were added slowly, keeping the temperature between 10 and 12° C. Once the addition ended, the temperature of the mixture obtained was left to go up to about 20° C., and it was kept under stirring for 2 hours between 15 and 20° C. A 4 mL aliquot of the crude reaction product was mixed at room temperature with 20 mL of isopropyl acetate, forming a solid that was isolated by means of filtration. The obtained solid was analyzed by means of the ultra high performance liquid chromatography-mass spectrometry technique (UPLC-MS) in Waters Acquity UPLC equipment coupled to a Xevo G2 Tof YCA290 CL22ID detector. FIG. 4 shows that a monoisotopic mass m/z value of 420.0550 was obtained for the signal having the highest percentage, corresponding to molecular formula $C_{18}H_{19}N_3O_4Br$.

Comparative Example 1. Obtaining (2S)-2-(fluorophenylmethoxycarbonylamino)-5-methoxy-5-oxo-pentanoic acid 15.5 g (96 mmol) of (2S)-2-amino-5-methoxy-5-oxo-pentanoic acid (Glu(OMe)—OH) were mixed with 220 mL of dichloromethane. The mixture was cooled at 0° C., and 20.9 g (192 mmol) of trimethylsilyl chloride were added, keeping the temperature between 0 and 5° C. 25.0 g (193 mmol) of N,N-diisopropylethylamine were then slowly added, keeping the temperature between 0 and 5° C. The resulting mixture was heated to the reflux temperature and kept under stirring for 1 hour and 30 minutes. The reaction mixture was cooled at a temperature of 0° C., and 24.9 mL (96 mmol) of fluorenylmethyl chloroformate were added at a temperature between 0 and 5° C. The resulting reaction mixture was kept at the indicated temperature for 30 minutes, and then for 1 hour and 30 minutes at a temperature of about 20° C.

The reaction mixture was concentrated with a vacuum, and 160 mL of an 8% aqueous sodium bicarbonate solution and 160 mL of isopropyl acetate were added. The aqueous phase was separated by means of decantation, and it was acidified to a pH of about 2 by means of a 37% aqueous HCl solution. The resulting aqueous phase was extracted with isopropyl acetate (3×100 mL). The solvent was distilled by means of a vacuum until obtaining a residue that crystallized into isopropanol, yielding 35.0 g (94.9%) of a white solid with a purity of 99.1% corresponding to (2S)-2-(fluorophenylmethoxycarbonylamino)-5-methoxy-5-oxo-pentanoic acid (Fmoc-Glu(OMe)—OH). The purity of the obtained products was analyzed by means of the ultra high performance liquid chromatography technique in Waters Acquity HClass equipment, equipped with a variable wave detector and temperature-controlled oven for the column.

Comparative Example 2. Obtaining (2S)-2-(fluorenyl-9-methoxycarbonylamino)-5-methoxy-5-oxo-pentanoic acid chloride 18.0 g (47 mmol) of (2S)-2-(fluorenyl-9-methoxycarbonylamino)-5-methoxy-5-oxo-pentanoic acid were dissolved in 126 mL of dichloromethane. The solution was cooled at a temperature of 20° C., and 0.25 mL of DMF and 6.7 g (56 mmol) of thionyl chloride were added. The resulting solution was kept under stirring at a temperature between 15 and 20° C. for 3 hours. The resulting mixture was subsequently concentrated by means of a vacuum to obtain, in a virtually quantitative manner, 19.5 g of a white solid corresponding to (2S)-2-(fluorenyl-9-methoxycarbonylamino)-5-methoxy-5-oxo-pentanoic acid chloride, which was used directly in the following reaction.

Comparative Example 3. Obtaining methyl (4S)-4-(fluorenyl-9-methoxycarbonylamino)-5-[4-bromo-2-(pyridine-2-carbonyl)aniline]-5-oxo-pentanoate of Formula (B1)

19.5 g (47 mmol) of (2S)-2-(fluorenyl-9-methoxycarbonylamino)-5-methoxy-5-oxo-pentanoic acid chloride obtained in the preceding step were dissolved in 90 mL of dichloromethane, and a previously prepared solution of 13.0 g (47 mmol) of (2-amino-5-bromophenyl)-pyridin-2-yl-methanone of formula (A) in 40 mL of dichloromethane was added at a temperature between 0 and 10° C. The obtained mixture was kept under stirring at the reflux temperature for 30 minutes.

Once the reaction ended, 100 mL of an 8% aqueous sodium bicarbonate solution and 100 mL of dichloromethane were added at a temperature of about 20° C. The organic phase was separated and concentrated by means of a vacuum to obtain a residue to which 150 mL of isopropanol were added. The mixture was cooled at about 15° C., and the resulting solid was filtered to obtain 27.5 g (91.7%) of a solid corresponding to methyl (4S)-4-(fluorenyl-9-methoxycarbonylamino)-5-[4-bromo-2-(pyridine-2-carbonyl)aniline]-5-oxo-pentanoate. The purity of the obtained products was analyzed by means of the ultra high performance liquid chromatography technique in Waters Acquity HClass equipment, equipped with a variable wave detector and temperature-controlled oven for the column.

Figure 5:
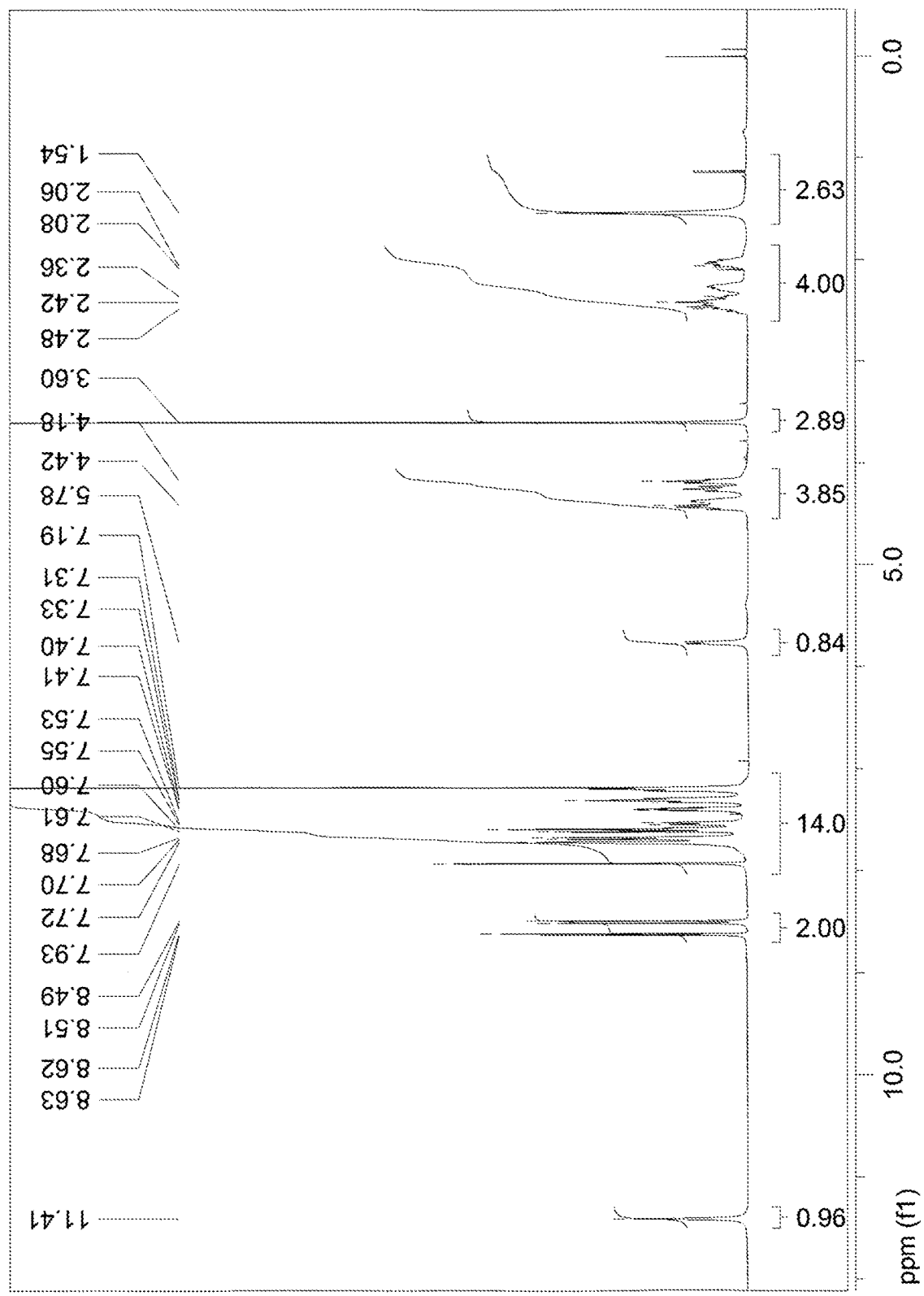
FIG. 5 shows the 1H-NMR of the compound of formula (B1).

FIG. 5 shows the 1H-NMR spectrum. 1H-NMR (CDCl$_3$, 400 MHz) δ(ppm): 11.41 (1H, s), 8.62 (1H, m), 8.50 (1H, d), 7.93 (1H, d), 7.72 (2H, m), 7.68 (2H, m), 7.61 (1H, d), 7.59 (1H, d), 7.54 (1H, d), 7.40 (1H, m), 7.31 (1H, t), 7.21 (1H, t), 5.77 (1H, d), 4.41 (2H, m), 4.26 (1H, t), 4.18 (1H, t), 3.63 (3H, s), 2.43 (2H, m), 2.27 (1H, m), 2.04 (1H, m)

Comparative Example 4. Obtaining 3-[(3S)-7-bromo-2-oxo-5-(pyridin-2-yl)-2,3-dihydro-1H-[1,4]-benzodiazepin-3-yl] propionic acid methyl ester of formula (D) from methyl (4S)-4-(fluorenyl-9-methoxycarbonylamino)-5-[4-bromo-2-(pyridine-2-carbonyl)aniline]-5-oxo-pentanoate 16.8 g (26 mmol) of methyl (4S)-4-(fluorenyl-9-methoxycarbonylamino)-5-[4-bromo-2-(pyridine-2-carbonyl)aniline]-5-oxo-pentanoate were dissolved in 80 mL of dichloromethane, and 48.8 g (482 mmol) of triethylamine were added. Once the addition ended, the obtained mixture was kept under stirring overnight at a temperature between 40 and 45° C.

Once it no longer had to be kept under the aforementioned conditions, the reaction mixture was concentrated by means of a vacuum to obtain a residue to which 40 mL of acetone were added. It was heated at reflux, obtaining a homogenous mixture which was cooled at a temperature of about 20° C. The resulting solid was filtered and washed with acetone, yielding a product that contained 62% 3-[(3S)-7-bromo-2- oxo-5-(pyridin-2-yl)-2,3-dihydro-1H-[1,4]-benzodiazepin-3-yl] propionic acid methyl ester of formula (D). This solid was recrystallized into isopropanol, obtaining 4.2 g (40%) of the desired product with a purity of 94%. The purity of the obtained products was analyzed by means of the ultra high performance liquid chromatography technique in Waters Acquity HClass equipment, equipped with a variable wave detector and temperature-controlled oven for the column.

Comparative Example 5. Obtaining bis-morpholinophosphorylchloride (BMPC)

25.0 g (16.30 mmol) of phosphorus oxychloride were dissolved in 100 mL of toluene under a nitrogen atmosphere. The resulting solution was cooled at a temperature of 0° C., and 5.7 g (65.44 mmol) of morpholinone were added to obtain a suspension that was kept under stirring at a temperature of about 0° C. for 1 hour and subsequently at a temperature of 20-25° C. for 1 additional hour. Once it no longer had to be kept under the aforementioned conditions, the salts resulting from the reaction were filtered and the toluene solution thus obtained was vacuum-distilled to an approximate solvent volume corresponding to half the initial volume used. The temperature of the resulting mixture was adjusted between 40 and 45° C., and said mixture was filtered through diatomaceous earth to obtain a colorless solution. The resulting toluene was distilled by means of a vacuum, and 135 mL of tetrahydrofuran were added to obtain a colorless solution containing 33.3 g of bis-morpholinophosphorylchloride (BMPC).

Comparative Example 6. Obtaining 3-[(3S)-7-bromo-2-(bis-morpholinophosphoryloxy)-5-(pyridin-2-yl)-[1,4]-benzodiazepin-3-yl]-propionic Acid Methyl Ester of Formula (E1) from the Compound of Formula (D)

5.5 g (13.67 mmol) of 3-[(3S)-7-bromo-2-oxo-5-(pyridin-2-yl)-2,3-dihydro-1H-[1,4]-benzodiazepin-3-yl] propionic acid methyl ester were dissolved in 30 mL of anhydrous tetrahydrofuran. 7 mL of a commercial 2M lithium diisopropylamide solution in a mixture of tetrahydrofuran and n-heptane were added slowly, keeping the temperature at about −25° C. and under a nitrogen atmosphere. Once the addition ended, the temperature was increased to −5° C., and 28 mL of a solution previously prepared according to the methodology described in Comparative Example 5, corresponding to 6.9 g (27.10 mmol) of bis-morpholinophosphorylchloride (BMPC), were added, maintaining said temperature. The obtained mixture was left to develop under stirring in a nitrogen atmosphere for 2 hours at a temperature of about −5° C., the total consumption of the starting product being verified by means of UPLC (ultra performance liquid chromatography).

Example 5. Obtaining (3S)-3-[7-bromo-2-(2,2-dimethoxypropylamino)-5-pyridin-2-yl-3H-benzo[e][1,4]diazepin-3-yl]propionic Acid Methyl Ester of Formula (E2) from the Compound of Formula (E1)

The precursor 2,2-dimethoxypropylamine can be prepared according to the methodology described, for example, in Cui, P. et al., *Bioorganic & Medicinal Chemistry Letters*, 2006, 16(13), 3401-3405. A previously prepared solution of 2,2-dimethoxypropylamine in anhydrous tetrahydrofuran (5.4 g of the amine (41.16 mmol) in 50 mL of the organic solvent) was slowly added at a temperature of −5° C. to the solution obtained according to the methodology described in Comparative Example 6. Once the addition ended, the temperature of the obtained mixture was increased to about 20° C., and it was kept under stirring for 16 hours at a temperature of about 20° C.

Once it no longer had to be kept under the aforementioned conditions, 50 mL of an 8% aqueous $NaHCO_3$ solution and 50 mL of 2-methyltetrahydrofuran were added. The resulting mixture was kept under stirring for about 5 minutes and the resulting organic phase containing (3S)-3-[7-bromo-2-(2,2-dimethoxypropylamino)-5-pyridin-2-yl-3H-benzo[e][1,4]diazepin-3-yl]propionic acid methyl ester was subsequently separated. The organic solvent was vacuum-distilled, and 50 mL of acetone were added to the resulting residue. The obtained mixture was heated at the reflux temperature and then slowly cooled to about 20° C. The resulting solid was filtered and oven-dried, finally obtaining 5.2 g (75.7% from 3-[(3S)-7-bromo-2-oxo-5-(pyridin-2-yl)-2,3-dihydro-1H-[1,4]-benzodiazepin-3-yl] propionic acid methyl ester of formula (D), with a purity of 98.5% by means of UPLC) of (3S)-3-[7-bromo-2-(2,2-dimethoxypropylamino)-5-pyridin-2-yl-3H-benzo[e][1,4]diazepin-3-yl] propionic acid methyl ester.

Figure 6:
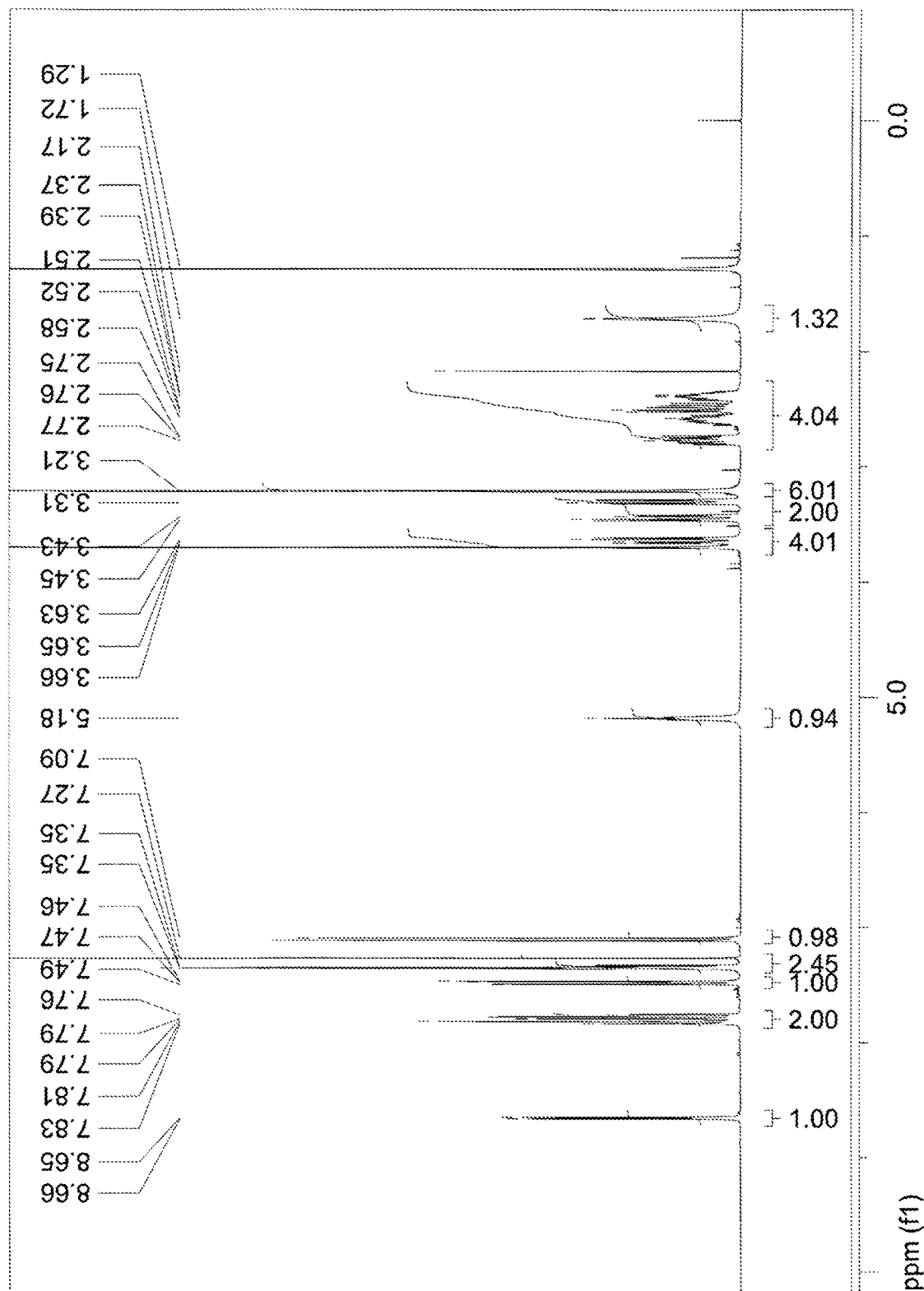
FIG. 6 shows the 1H-NMR of the compound of formula (E2).

FIG. 6 shows the 1H-NMR spectrum. 1H-NMR ($CDCl_3$, 400 MHz) δ(ppm): 8.65 (1H, d), 7.79 (2H, m), 7.48 (1H, dd), 7.35 (2H, m), 7.10 (1H, d), 5.18 (1H, m), 3.70 (3H, s), 3.64 (1H, dd), 3.45 (1H, dd), 3.31 (1H, dd), 3.22 (3H, s), 3.21 (3H, s), 2.77 (1H,m), 2.65-2.37 (3H, m), 1.72 (1H, s), 1.29 (3H, s).

Figure 7:
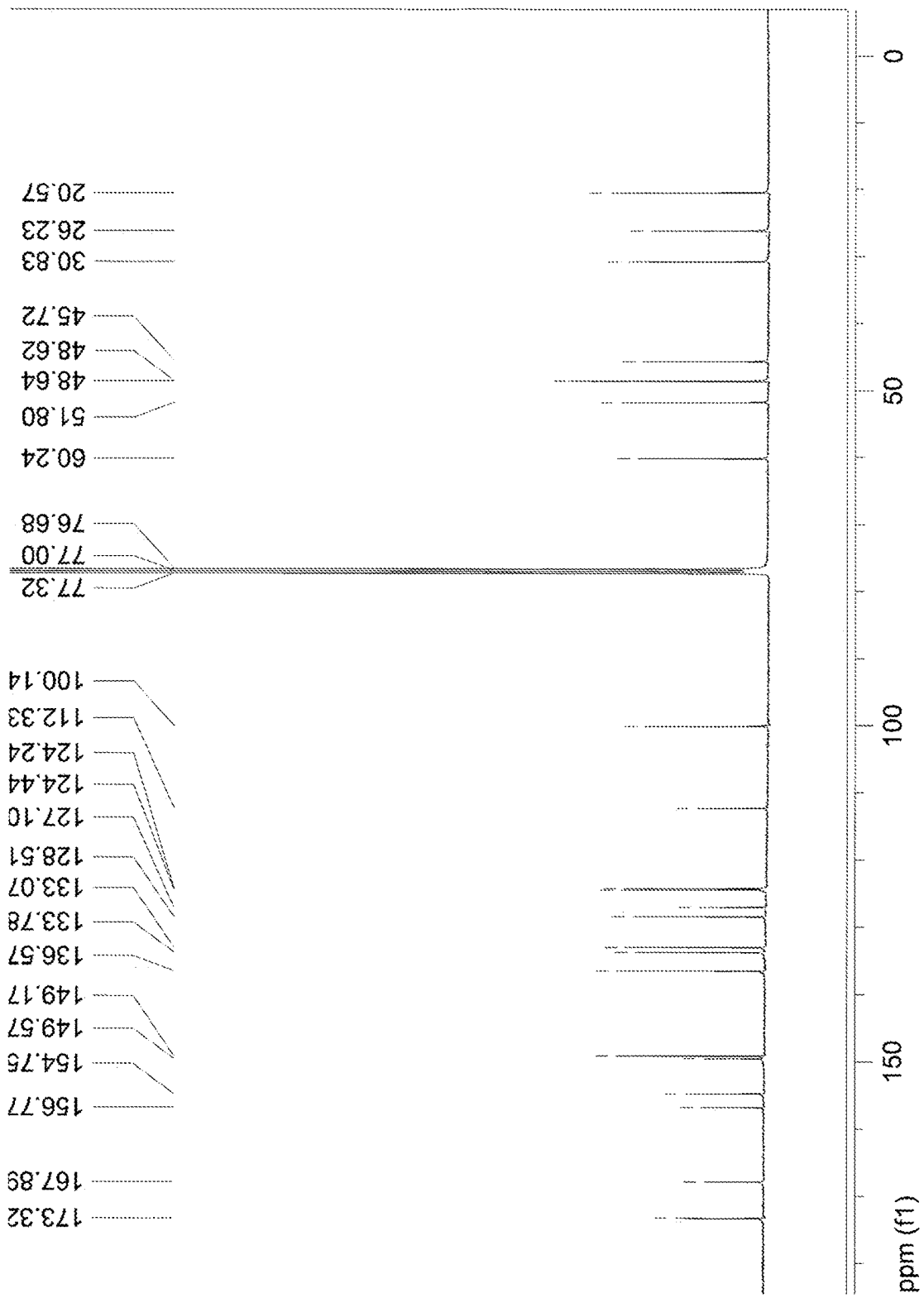
FIG. 7 shows the 13C-NMR of the compound of formula (E2).

FIG. 7 shows the 13C-NMR spectrum. 13C-NMR ($CDCl_3$, 400 MHz) δ(ppm): 173.31, 167.89, 156.77, 154.75, 149.57, 149.16, 136.57, 133.78, 133.07, 128.51, 127.10, 124.44, 124.24, 112.33, 100.14, 60.24, 51.80, 48.65, 48.62, 45.72, 30.84, 26.23, 20.57.

Example 6. Obtaining the benzenesulfonic acid salt of 3-[(4S)-8-bromo-1-methyl-6-(pyridin-2-yl)-4H-imidazo[1,2-a][1,4]benzodiazepin-4-yl]-propionic Acid Methyl Ester from the Compound of Formula (E2)

19 g (37.81 mmol) of (3S)-3-[7-bromo-2-(2,2-dimethoxypropylamino)-5-pyridin-2-yl-3H-benzo[e][1,4]diazepin-3-yl]propionic acid methyl ester were suspended in 40 mL of acetone under a nitrogen atmosphere. A previously obtained solution of 6.0 g (37.97 mmol) of benzenesulfonic acid in acetone was added, keeping the temperature at about 20° C. A completely clear orange solution that is kept under stirring in a nitrogen atmosphere for 2 hours at a temperature of about 20° C. was thereby obtained. The resulting mixture containing a crystalline solid was subsequently cooled at 0° C., and said crystalline solid was filtered and oven-dried, finally obtaining 7.1 g (60%) of a white crystalline solid corresponding to the besylate salt of 3-[(4S)-8-bromo-1-methyl-6-(pyridin-2-yl)-4H-imidazo[1,2-a][1,4]benzodiazepin-4-yl]-propionic acid methyl ester with a purity of 99.8% by means of UPLC.

Figure 8:
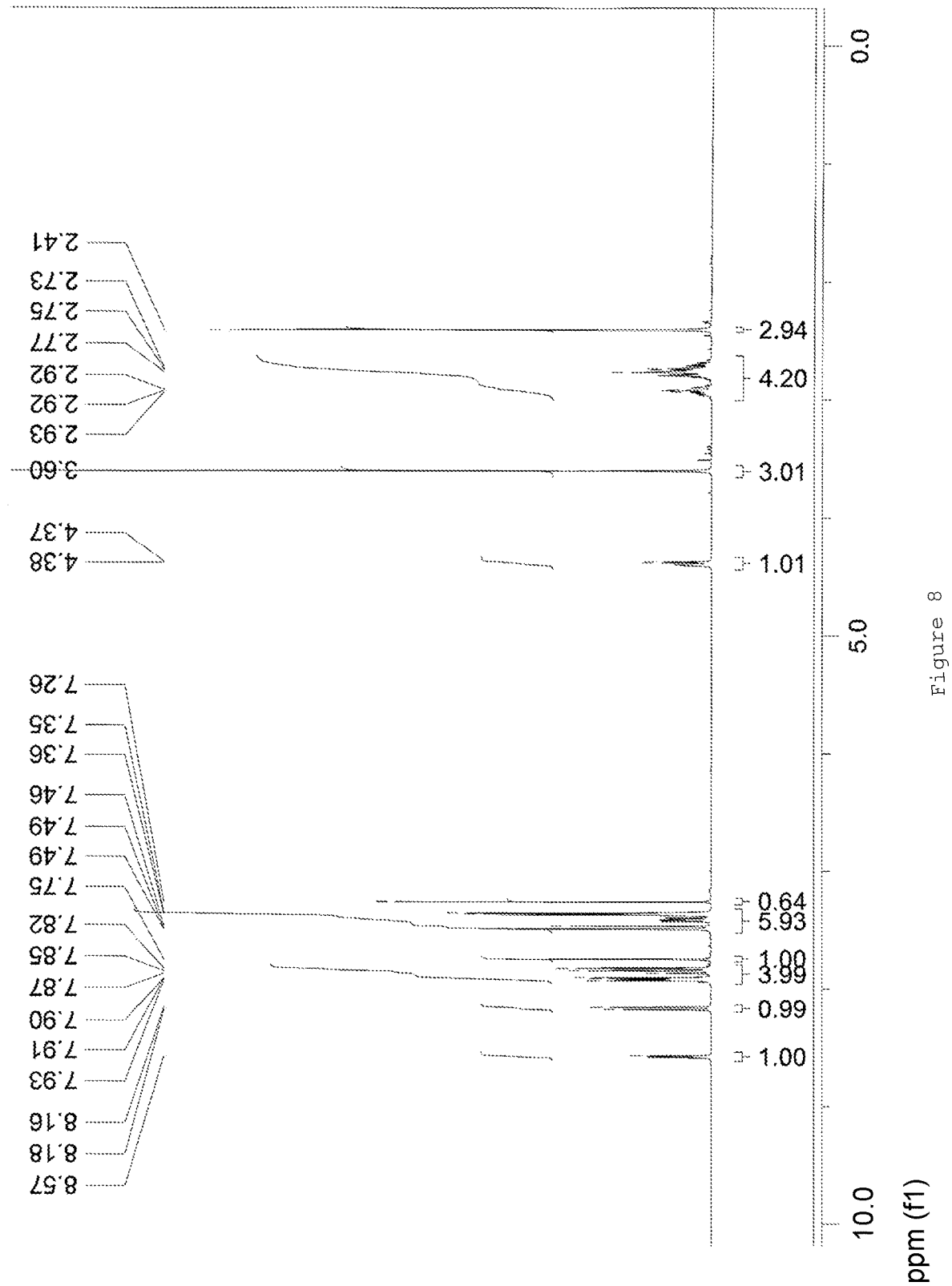
FIG. 8 shows the 1H-NMR of the compound of formula (F).

FIG. 8 shows the 1H-NMR spectrum. 1H-NMR ($CDCl_3$, 400 MHz) δ(ppm): 8.57 (1H, d), 8.17 (1H, d), 7.91 (2H, m), 7.85 (2H, m), 7.74 (1H, d), 7.48 (2H, m), 7.41 (1H, dd), 7.36 (3H, m), 4.39 (1H, m), 3.60 (3H, s), 2.92 (1H, m), 2.74 (3H, m), 2.41 (3H, s).

Figure 9:
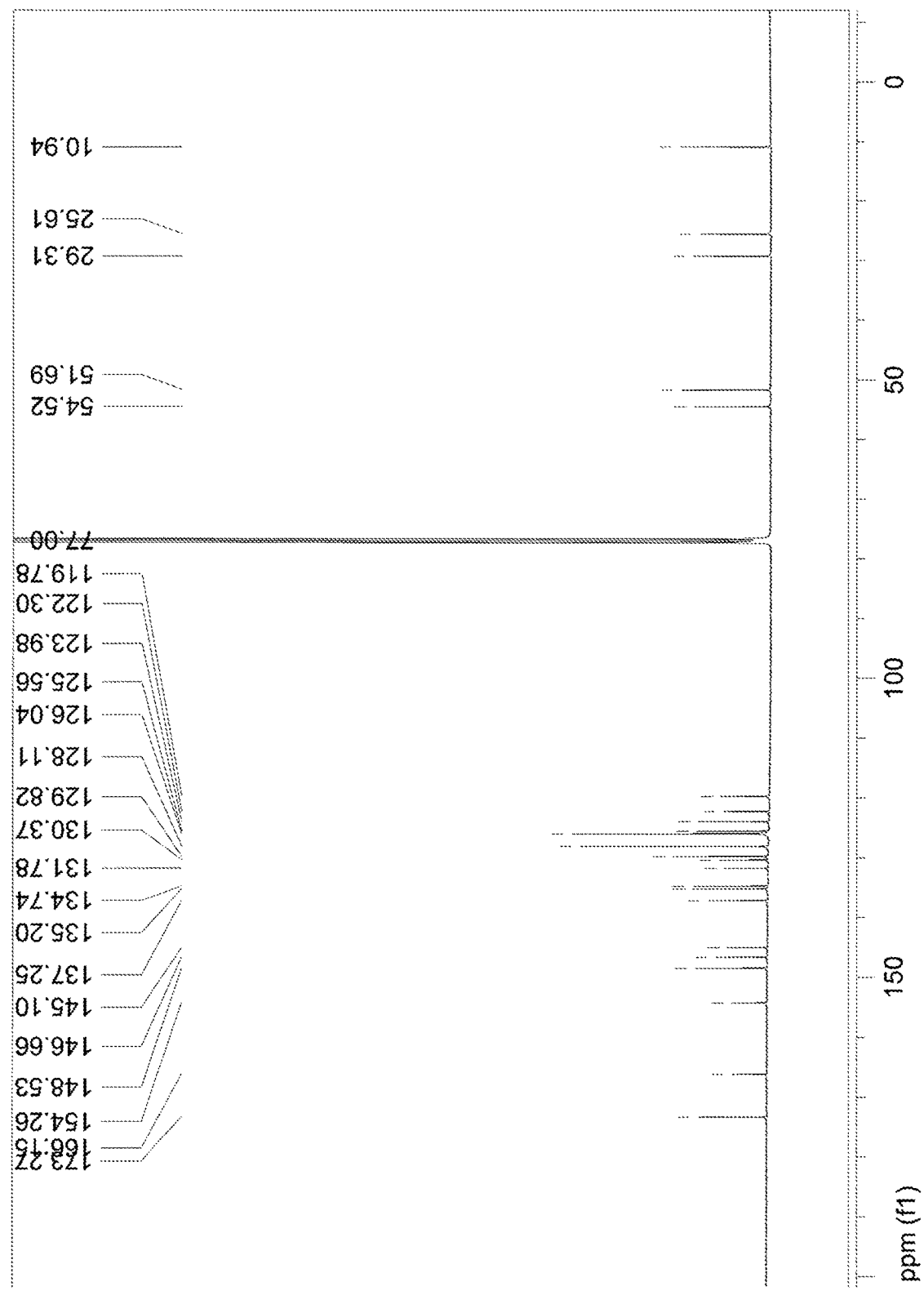
FIG. 9 shows the 13C-NMR of the compound of formula (F).

FIG. 9 shows the 13C-NMR spectrum. 13C-NMR ($CDCl_3$, 400 MHz) δ(ppm): 173.27, 166.15, 154.26, 148.53, 146.66, 145.10, 137.25, 135.21, 134.74, 131.78, 130.37, 129.82, 129.77, 128.11, 126.04, 125.91, 125.56, 123.98, 122.30, 119.78, 54.52, 51.70, 29.32, 25.62, 10.95.

The crystalline form obtained by means of the described example has been identified by means of its corresponding X-ray diffraction patterns (XRPD) and differential scanning calorimetry (DSC). XRPD analysis was conducted in a Siemens D-500 X-ray powder diffractometer equipped with a copper anode. Scanning parameters: 4-50 degrees 2θ, continuous scanning, ratio: 1.2 degrees/minute. DSC analysis was conducted in a Mettler Toledo 822e apparatus with STARe SW11.00 software. Parameters: heating range of 25 to 300° C. with a rate of 20° C./min and N$_2$ flow of 50 ml/min. The measurement is taken with a perforated closed capsule.

Figure 10:
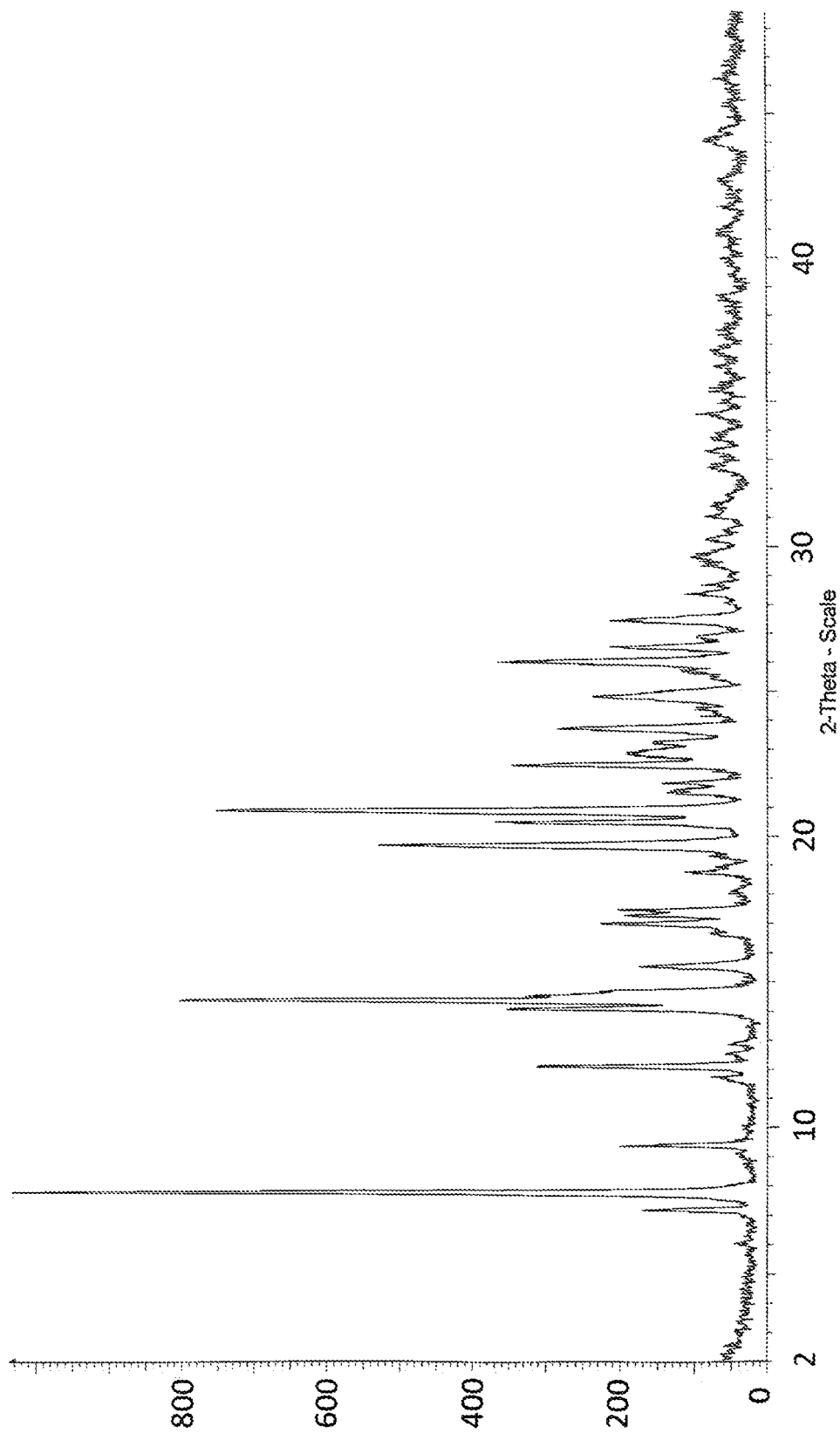
FIG. 10 shows the XRPD pattern of the compound of formula (F).
Figure 11:
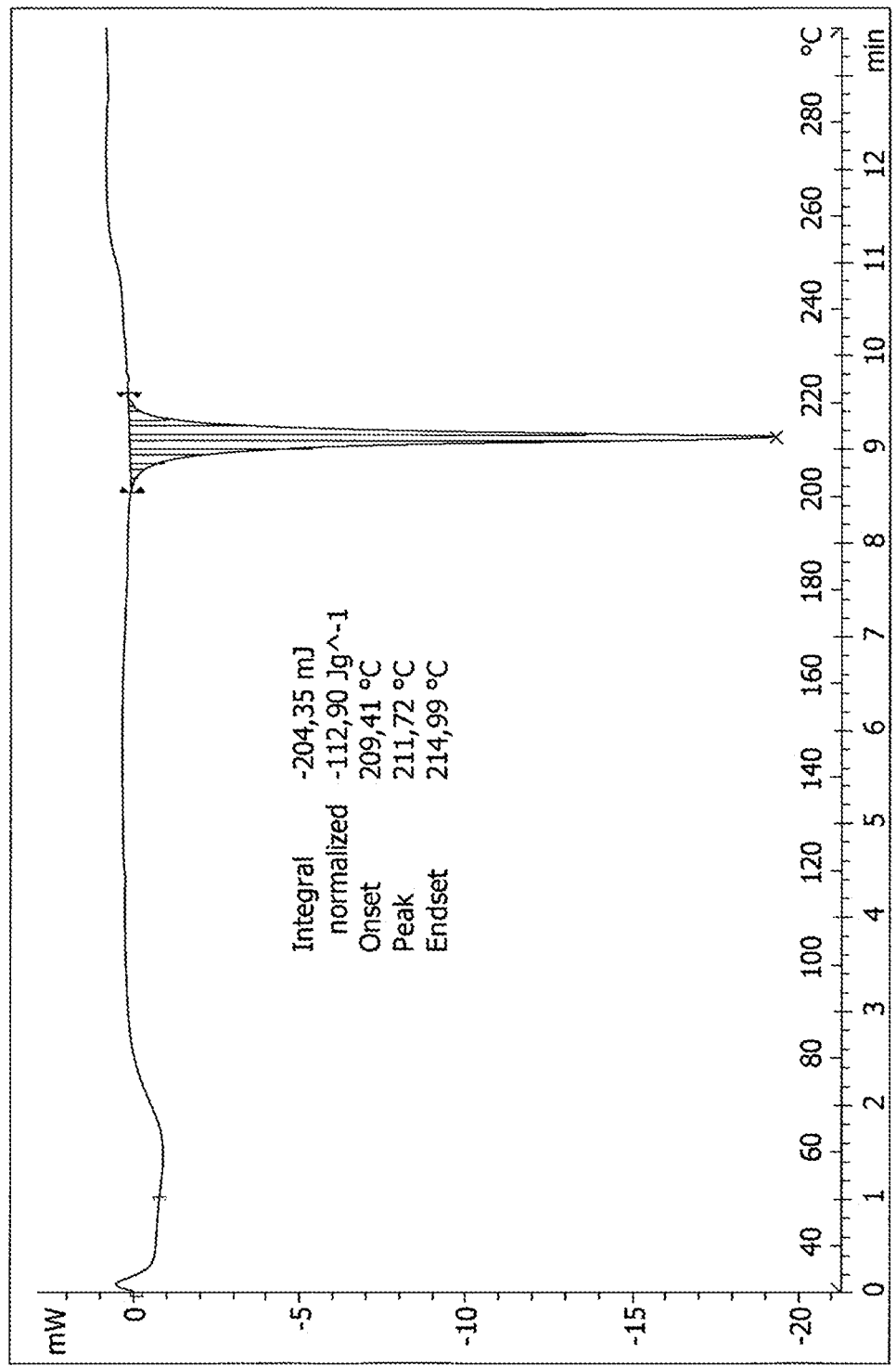
FIG. 11 shows the DSC pattern of the compound of formula (F).

FIGS. 10 and 11 show the XRPD and DSC patterns, respectively, obtained for the besylate salt of 3-[(4S)-8-bromo-1-methyl-6-(pyridin-2-yl)-4H-imidazo[1,2-a] [1,4]benzodiazepin-4-yl]-propionic acid methyl ester.

Example 7. Obtaining the benzenesulfonic acid salt of 3-[(4S)-8-bromo-1-methyl-6-(pyridin-2-yl)-4H-imidazo[1,2-a] [1,4]benzodiazepin-4-yl]-propionic acid methyl ester 52 g (104 mmol) of (3S)-3-[7-bromo-2-(2,2-dimethoxypropylamino)-5-pyridin-2-yl-3H-benzo[e] [1,4]diazepin-3-yl] propionic acid methyl ester (99.1% purity as determined by UPLC) were suspended in 310 mL of acetone under a nitrogen atmosphere. A previously obtained solution of 18 g (0.102 mmol) of benzenesulfonic acid 90% in 52 ml of acetone was added, keeping the temperature at about 20° C. A completely clear orange solution that is kept under stirring in a nitrogen atmosphere for 2 hours at a temperature of about 25° C. was thereby obtained. The resulting suspension was then heated to a temperature between 45 and 50° C., and kept under stirring for 1 hour. The resulting mixture was subsequently cooled to a temperature of about 20° C., and the resulting solid was filtered and oven-dried, finally obtaining 52.55 g (84.5%) of a white crystalline solid corresponding to the besylate salt of 3-[(4S)-8-bromo-1-methyl-6-(pyridin-2-yl)-4H-imidazo[1,2-a] [1,4]benzodiazepin-4-yl]-propionic acid methyl ester with a purity of 99.6% by means of UHPLC.

The invention claimed is:

1. A method for preparing a besylate salt of 3-[(4S)-8-bromo-1-methyl-6-(pyridin-2-yl)-4H-imidazo[1,2-a][1,4]benzodiazepin-4-yl]-propionic acid methyl ester of formula (F),

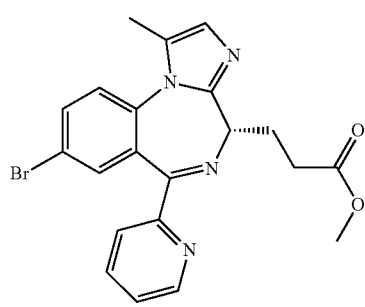

characterized in that it comprises a step of reacting a compound of formula (E),

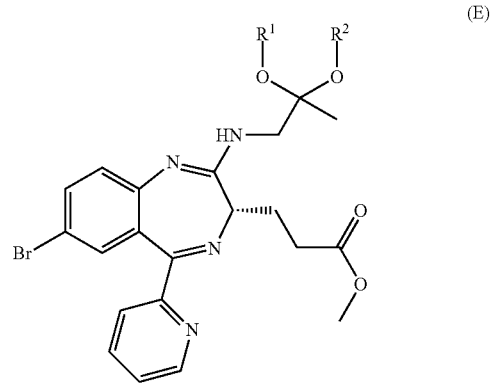

wherein $R^1$ and $R^2$ are independently selected from a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl; or wherein R', together with $R^2$, forms a residue of formula —CH$_2$—(CR$^3$R$^4$)$_n$—CH$_2$—, wherein n is equal to 0, 1, 2, 3, or 4, and wherein $R^3$ and $R^4$ are independently selected from a hydrogen or a linear or branched C1-C6 alkyl optionally substituted with 1, 2, or 3 groups selected from linear or branched C1-C3 alkyl, halogen, amino, alkylamino, or OR', wherein R' represents an H or a linear or branched C1-C6 alkyl;

with a benzenesulfonic acid;

in an organic solvent selected from esters, alcohols, and ketones.

2. The method according to claim 1, characterized in that the compound of formula (E) is prepared by reacting the compound of formula (DE)

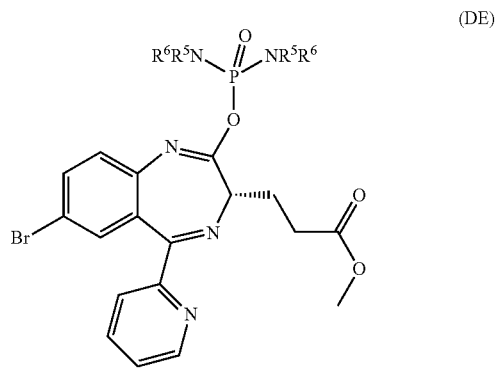

wherein $R^5$ and $R^6$ are independently selected from a linear or branched C1-C4 alkyl optionally substituted with 1, 2, or 3 groups selected from linear or branched C1-C3 alkyl, halogen, amino, alkylamino, or OR', wherein R' represents an H or a linear or branched C1-C6 alkyl; or when $R^5$ and $R^6$ adjacent to one another form a saturated 4- to 7-membered heterocycle with the nitrogen to which they are bound, and wherein the heterocycle optionally contains 1, 2, or 3 heteroatoms selected from N and O;

with a primary amine of formula

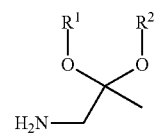

wherein R¹ and R² are as defined in claim 1;
in an anhydrous organic solvent selected from cyclic esters.
3. The method according to claim 2, wherein the compound of formula (E) comprises (3 S)-3-[7-bromo-2-(2,2-dimethoxypropylamino)-5-pyridin-2-yl-3H-benzo[e][1,4]diazepin-3-yl]propionic acid methyl ester
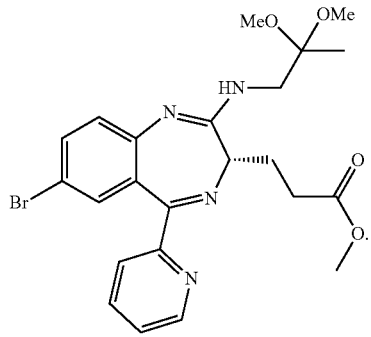 [SMILES: COC(=O)CC[C@@H]1N=C(c2ccccn2)c2cc(Br)ccc2N=C1NCC(C)(OC)OC]
4. The method according to claim 2, wherein the compound of formula (DE) comprises
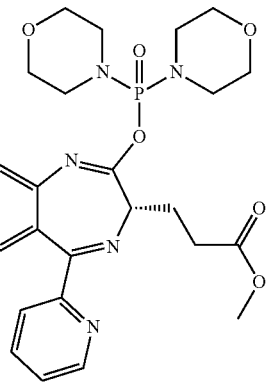
* * * * *